United States Patent
Lo et al.

(10) Patent No.: US 11,986,653 B2
(45) Date of Patent: *May 21, 2024

(54) WIRELESS IMPLANT FOR MOTOR FUNCTION RECOVERY AFTER SPINAL CORD INJURY

(71) Applicant: THE REGENTS OF THE UNIVERSITY OF CALIFORNIA, Oakland, CA (US)

(72) Inventors: Yi-Kai Lo, Los Angeles, CA (US); Wentai Liu, Los Angeles, CA (US); Victor R. Edgerton, Los Angeles, CA (US); Chih-Wei Chang, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 239 days.

This patent is subject to a terminal disclaimer.

(21) Appl. No.: 17/459,483

(22) Filed: Aug. 27, 2021

(65) Prior Publication Data
US 2022/0016420 A1    Jan. 20, 2022

Related U.S. Application Data

(60) Division of application No. 16/043,414, filed on Jul. 24, 2018, now Pat. No. 11,129,983, which is a
(Continued)

(51) Int. Cl.
*A61N 1/36* (2006.01)
*A61N 1/05* (2006.01)
(Continued)

(52) U.S. Cl.
CPC ....... *A61N 1/36003* (2013.01); *A61N 1/0551* (2013.01); *A61N 1/3787* (2013.01); *A61N 1/08* (2013.01)

(58) Field of Classification Search
CPC .............. A61N 1/36003; A61N 1/0551; A61N 1/3787; A61N 1/08
See application file for complete search history.

(56) References Cited

U.S. PATENT DOCUMENTS

| | | |
|---|---|---|
| 5,284,151 A | 2/1994 | Onoda |
| 5,630,836 A | 5/1997 | Prem |

(Continued)

FOREIGN PATENT DOCUMENTS

| | | |
|---|---|---|
| EP | 1303332 B1 | 4/2003 |
| WO | 2012129574 A2 | 9/2012 |
| WO | 2012129574 A3 | 9/2012 |

OTHER PUBLICATIONS

Korean Intellectual Property Office (KIPO), international search report and written opinion dated May 8, 2017, related PCT international application No. PCT/US2017/015435, pp. 1-11, claims searched, pp. 12-15.

(Continued)

*Primary Examiner* — Mark W. Bockelman
(74) *Attorney, Agent, or Firm* — O'BANION & RITCHEY LLP; John P. O'Banion

(57) ABSTRACT

A wireless implant and associated system for motor function recovery after spinal cord injury, and more particularly a multi-channel wireless implant with small package size. The wireless implant can further be used in various medical applications, such as retinal prostheses, gastrointestinal implant, vagus nerve stimulation, and cortical neuromodulation. The system also includes a method and its implementation to acquire the impedance model of the electrode-tissue interface of the implant.

10 Claims, 15 Drawing Sheets

Related U.S. Application Data continuation of application No. PCT/US2017/015435, filed on Jan. 27, 2017.

(60) Provisional application No. 62/287,584, filed on Jan. 27, 2016.

(51) Int. Cl.
*A61N 1/08* (2006.01)
*A61N 1/378* (2006.01)

(56) References Cited

U.S. PATENT DOCUMENTS

| | | |
|---|---|---|
| 6,490,486 B1 | 12/2002 | Bradley |
| 8,224,453 B2 | 7/2012 | De Ridder |
| 9,101,769 B2 | 8/2015 | Edgerton |
| 9,409,023 B2 | 8/2016 | Burdick |
| 11,129,983 B2 | 9/2021 | Lo |
| 2005/0080460 A1 | 4/2005 | Wang |
| 2009/0157141 A1 | 6/2009 | Chiao |
| 2011/0224755 A1 | 9/2011 | Arle |
| 2014/0180361 A1 | 6/2014 | Burdick |

OTHER PUBLICATIONS

European Patent Office (EPO), supplementary European search report dated Aug. 13, 2019, related European patent application No. 17745012.9, pp. 1-8, claims searched, pp. 9-12.

WIRELESS IMPLANT FOR MOTOR FUNCTION RECOVERY AFTER SPINAL CORD INJURY

CROSS-REFERENCE TO RELATED APPLICATIONS

This application is a division of U.S. patent application Ser. No. 16/043,414 filed on Jul. 24, 2018, incorporated herein by reference in its entirety, which is a 35 U.S.C. § 111(a) continuation of PCT international application number PCT/US2017/015435 filed on Jan. 27, 2017, incorporated herein by reference in its entirety, which claims priority to, and the benefit of, U.S. provisional patent application Ser. No. 62/287,584 filed on Jan. 27, 2016, incorporated herein by reference in its entirety. Priority is claimed to each of the foregoing applications.

The above-referenced PCT international application was published as PCT International Publication No. WO 2017/132566 on Aug. 3, 2017, which publication is incorporated herein by reference in its entirety.

STATEMENT REGARDING FEDERALLY SPONSORED RESEARCH OR DEVELOPMENT

This invention was made with Government support under EB007615, awarded by the National Institutes of Health. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to an implantable stimulation device, and more particularly to a wireless implant for motor function recovery.

2. Background Discussion

Epidural spinal stimulation has shown effectiveness in recovering the motor function of spinal cord transected rats and patients with spinal cord injury (SCI) by modulating neural networks in lumbosacral spinal segments. Through stimulation, paralyzed subjects are able to perform weight-bearing standing and stepping. Current implants that are adopted for SCI patients are generally dedicated for pain reduction, and perform blind stimulation with limited stimulation flexibility and have a bulky form factor. It is preferable that the implant package has a comparable size to its bioelectronics and a high-density stimulator to support stimulation with high spatial resolution. Miniaturization of the form factor of the implant reduces the surgical invasiveness. Notably, this capability has not been achieved and reported in existing devices.

Measuring the electrode-tissue impedance is also critical to ensure safe stimulation. Commercial implants adopt a specific signal generator to estimate the impedance by injecting a small sinusoidal signal at a fixed frequency into the electrode and by measuring the resulting electrode voltage. However, this approach provides very limited information as the estimated impedance only informs the reliability of the electrode or its proximity to the targeted tissue/neurons. Moreover, this impedance estimation is merely suitable to characterize electrode for recording purposes, as it is based on small signal analysis, while a large transient voltage is imposed on the electrode during stimulation.

BRIEF SUMMARY

The technology described herein comprises a wireless implant for motor function recovery after spinal cord injury, and more particularly a multi-channel wireless implant with small package size. The wireless implant can further be used in various medical applications, such as retinal prostheses, gastrointestinal implant, vagus nerve stimulation, cortical neuromodulation, or use with stroke patients. The systems and methods of the present description also include a method and its implementation to acquire the impedance model of the electrode-tissue interface.

High-density stimulation not only allows the steering of injected electrical charge to improve stimulation efficiency and efficacy, but also provides the flexibility to uncover the optimal stimulation sites for each individual subject. Furthermore, the epidural electrode is configured to by soft and flexible because a mechanical mismatch, which leads to neuroinflammatory responses at the chronic stage, exists at the tissue-electrode interface.

In contrast to stimulation with pre-loaded patterns, the motor-function recovery implant of the present description is configured to adaptively adjust its stimulation patterns at run time in response to the subject's varying physiological states. This is important because the activation of limb movement is associated with the spatial and temporal firings of motor neurons and the constant varying proprietary sensory feedback. It is thus a premise of the present description that selectively activating the spinal cord with carefully designed stimulation patterns that integrate both spatial and temporal structure along with sensory feedback information (i.e. muscle EMG and spinal field potential) improves the stimulation efficacy and quality of subject movements.

Deriving the equivalent circuit model of the electrode-tissue interface determines the safe stimulation boundary (i.e. pulse width and intensity) to ensure the electrode over potential is within the water window and the process of reversible reduction and oxidation across the electrode-electrolyte interface.

In one embodiment, the SoC implant of the present description targets motor function recovery after spinal cord injury. Its versatile functionalities and highly compact form factor (0.5 $cm^3$ and 0.7 g) also make it applicable in future implants for various medical applications.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
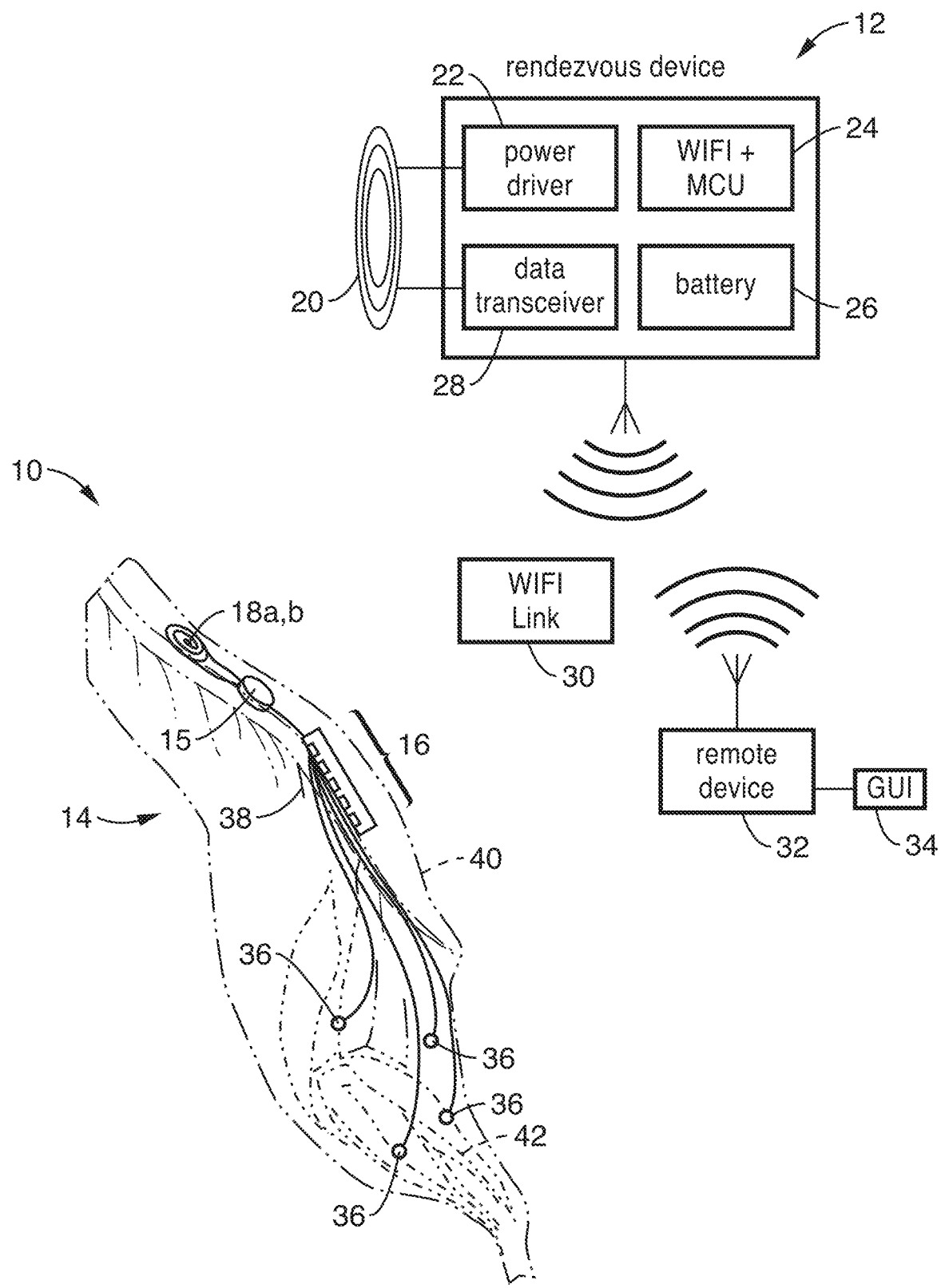
FIG. 1 is a schematic view of the implantable system and the biological mechanism for motor function recovery.

FIG. 1 illustrates an implantable system 10 for performing simultaneous stimulation and full-duplex data telemetry. System 10 comprises the following primary components: implant 14 configured to be disposed beneath skin 40 at or near a treatment location 38 (injured segment) of the spine, an external circuit or rendezvous device 12 configured to be worn by the patient to wirelessly power the implant 14 and link the implant 14 and a remote device 32 (e.g. smart phone/tablet, laptop or like computing device).

The implant 14 preferably comprises a miniaturized (e.g. 0.5 cm$^3$ and 0.7 g package) on chip (SoC) 15 configuration. A thin (8 µm), flexible polyimide based platinum electrode array 16 is placed into the epidural space for neural stimulation, and EMG (electromyography) wire electrodes 36 (e.g. AS632 Cooner wire, Chatsworth CA) are attached onto leg muscles 42. The size, pitch, and number of electrodes in the electrode array 16 may vary by application or location/placement of the implant within the body 14.

Figure 2:
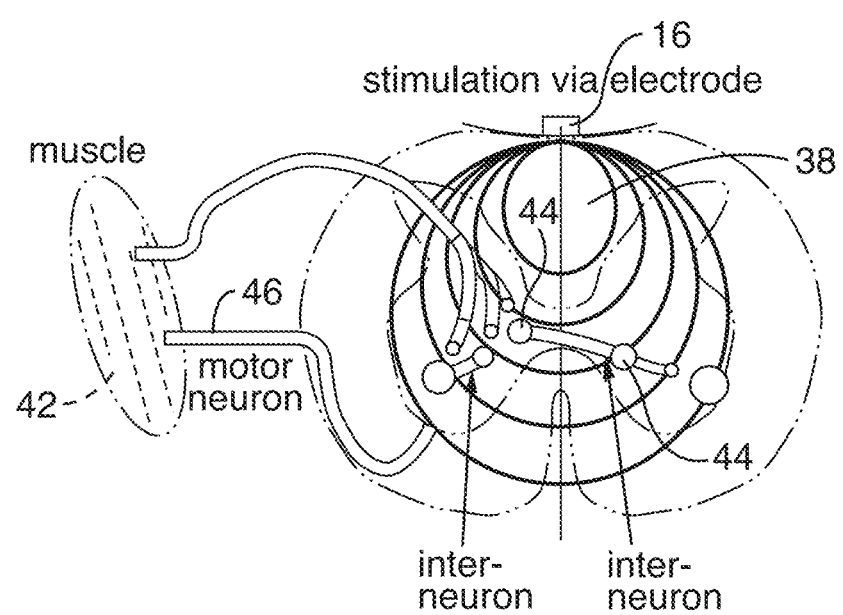
FIG. 2 is a diagram illustrating motor function activation by epidural electrical stimulation.

The core of the implant is a mixed-signal, multi-voltage SoC 15, which is configured to perform high-voltage (HV) 160-channel current stimulation, 16-channel recording, and 48-channel bio-impedance characterization with fully integrated power/data telemetry (see FIG. 2).

Figure 3A:
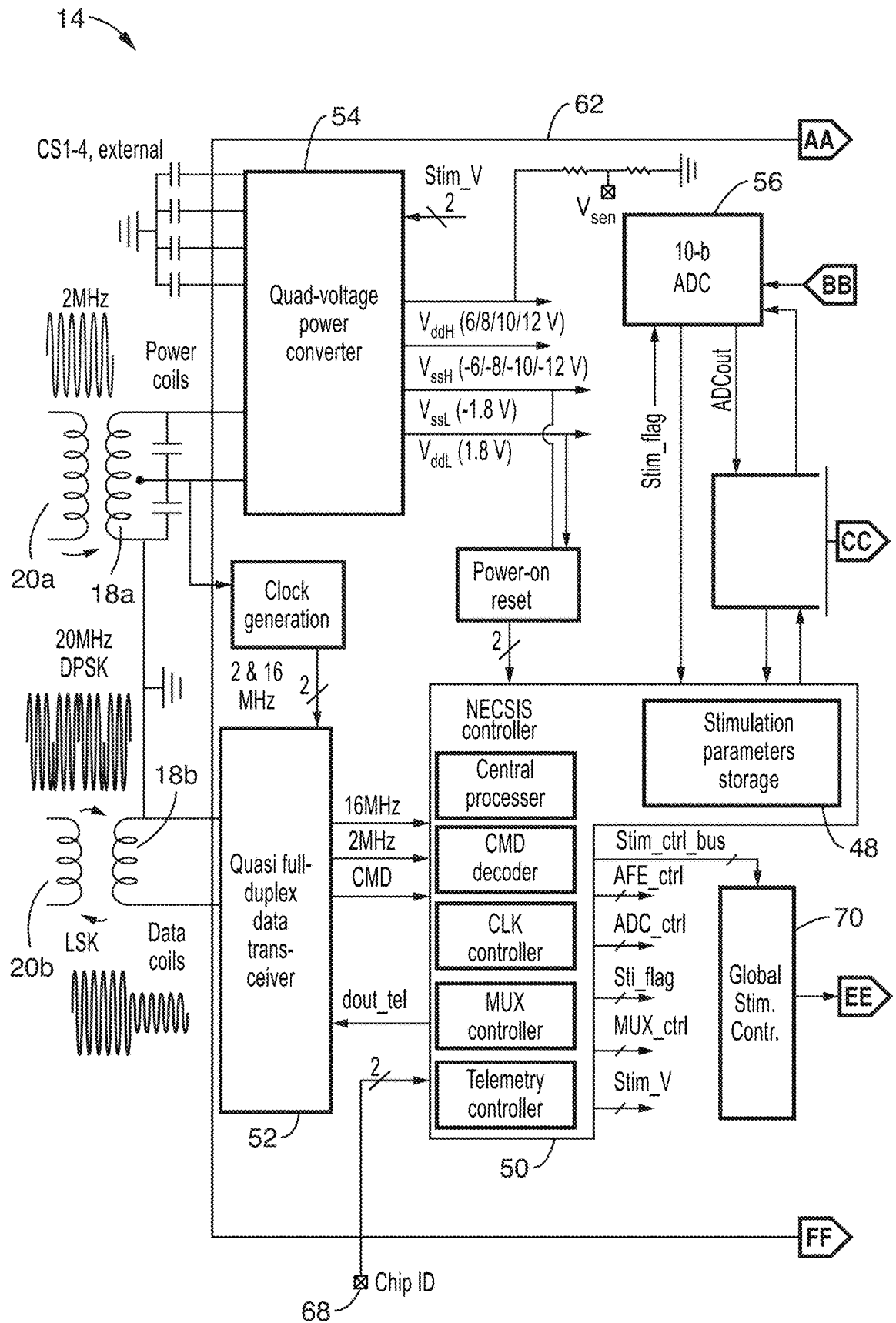
FIG. 3A and FIG. 3B show a system schematic wiring diagram of the SoC of the present description.

The implant 14 and the rendezvous device 12 are linked inductively via respective data and power coils 18a and 18b on the implant 14 and coils 20 on the rendezvous device. While coils 20 are shown as a singular unit in FIG. 1, they may also comprise respective data and power coils (20a and 20b) as shown in FIG. 3A.

The rendezvous device 12, is configured to be worn adjacent the patient's skin proximal to the implant 14, and comprises a data transceiver 28, power diverter 22, and WIFI/MCU circuitry, along with a battery 26 providing power to the circuitry. The data transceiver 28 and power driver 22 are coupled to coil 20 for wirelessly communicating with and powering implant 14. While communication between the rendezvous device 12 is shown as a WIFI connection, it is appreciated that other wireless (e.g. Bluetooth, etc.) or wired communication may be implemented. The external device 32 comprises software (e.g. cell phone application or the like) with a GUI 34 allowing user interface with the rendezvous device 12 and implant 14 over WIFI link 30.

FIG. 2 is a diagram illustrating a mechanism for motor function activation by epidural electrical stimulation as provided by the flexible electrode array 16. Complex neural networks residing in a target spinal segment can function to produce alternating motor patterns, which can be further alternated through the sensory feedback. For example, one's walking gait can be alternated unconsciously when stepping from a flat surface to a bumpy one. Motor function of the paralyzed patient may be activated to reengage the affected spinal segment 38 (e.g. lumbar sacral or cervical segment depending on the injured segment) by epidural electrical stimulation of inter-neurons 44 as well as motor-neurons 46 and sensory-neurons connecting the brain and spinal cord to reengage the neural network. Motor neurons 46 (motoneurons), carrying signals from the central nervous system (inter-neurons 44) to the outer parts (e.g. muscles 42, skin, glands) of the body, may now be engaged. EMG electrodes 36 at specific muscle 42 locations (e.g. leg or arm muscles) may be used to provide feedback with respect to motor neuron 46 engagement. By selectively activating the targeted region 38 of the spinal cord with carefully designed stimulation patterns that integrate both spatial and temporal structure, along with sensory feedback information (i.e. muscle 43 EMG 36 readings) the stimulation efficacy of the subject's neural network is improved, and thus the quality of subject's movements.

Figure 3B:
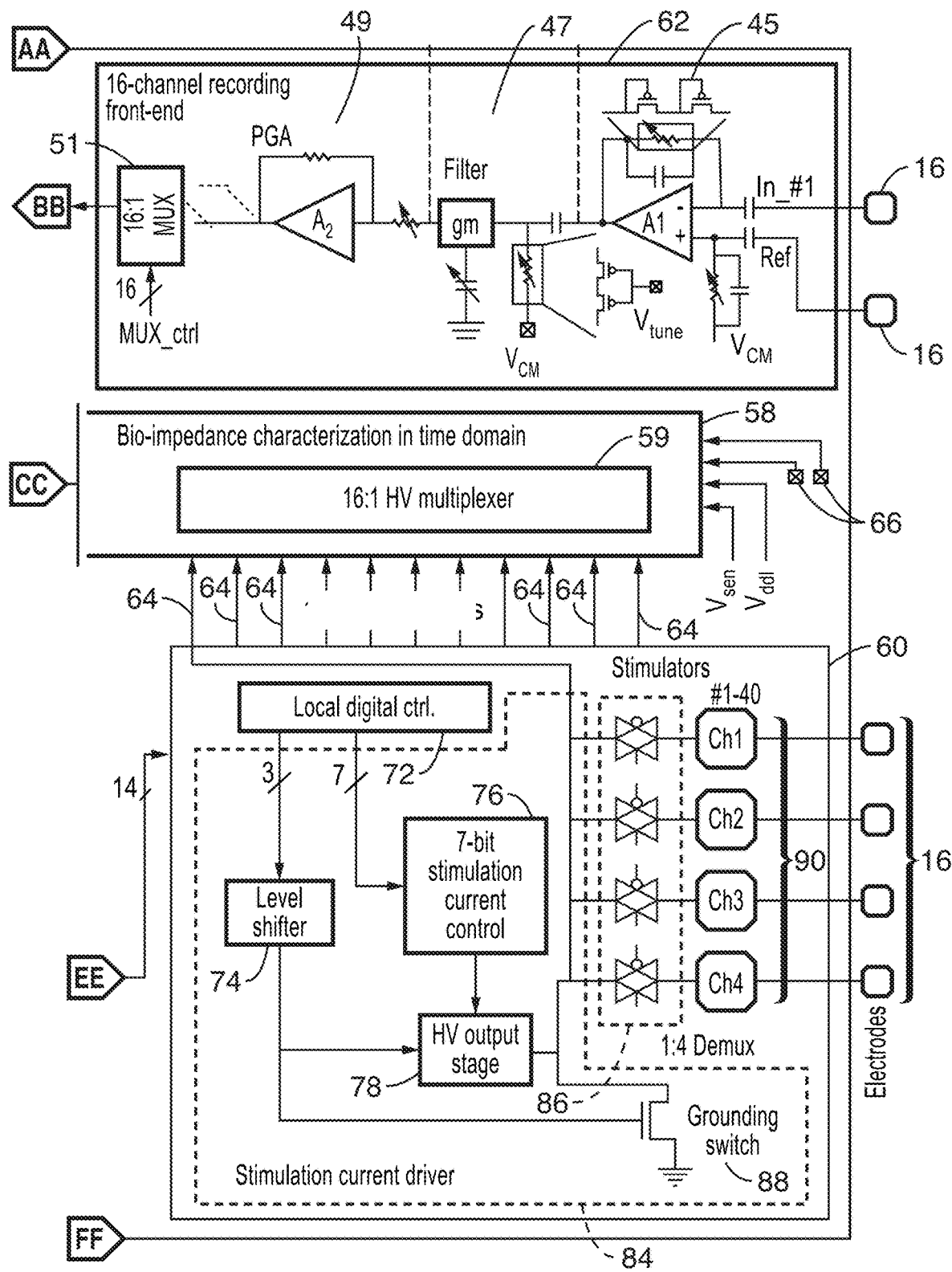

FIG. 3 and FIG. 3B show a system schematic wiring diagram of the implant 14 and SoC 15 of the present description. A multi-voltage power converter 54, data transceiver 52, NECSIS controller 50, neural stimulators 60, front-end 62 and impedance characterization 58 circuits are all integrated in the SoC 15. In a preferred embodiment, the power converter 54 generates 4 different voltages to power the implant, with added capability of adjusting the supply voltages for stimulators (e.g. ±6/8/10/12 V) to accommodate various bio-impedances. The supply voltages can be set by changing the voltage reference circuits in the power converter and can be varied based on different applications.

In one embodiment, the supply voltages are wirelessly programmable (e.g. via wireless device 32 and GUI 34). Given the known stimulation current and by measuring the electrode impedance, the supply voltage can be determined by the user to reduce power consumption of the implant 14. For example, for a user specified stimulus with intensity of 0.5 mA and short pulse width as well as the measured tissue resistance of 10 kHz, the minimal required compliance voltage is thus >±5V, greatly saving power consumption compared with setting supply voltages to ±12V. This compliance voltage may be continuously varied based on different stimulation parameters 68 and the electrode-tissue interface impedance. This is an important feature, as different electrode sizes and stimulation parameters are required for different biomedical application. This tunable capability can optimize the over system power consumption.

A quasi full-duplex data transceiver 52 links the SoC 15 and the rendezvous device 12 at 2 Mb/s (the data rate has been tested from 100 kbps to 4 Mbps) through an inductive data link. A processor/controller 50 (e.g. NECSIS (Neural Command Signal Interface System) controller) controls the implant 14 operation based on the received commands (CMDs 110—see FIG. 4). Stimulation of a plurality of channels 90 (e.g. 160 channels in the tested configuration) is achieved by 40 neural stimulators 60 each comprising stimulation current drivers 84, corresponding demultiplexer 86 (e.g. 1:4 Demux), and local digital control 72. The use of the Demux 86 expands the number of stimulation channels 90 without increasing the number of stimulation drivers 40, saving active chip area. The current driver 84 of each stimulator 60 is depicted in this example as comprising a level shifter 74 for translating logic levels for controlling a high voltage (HV) output stage 78, and grounding switch 88. Bits from local control circuit 72 also drive a stimulation current control circuit (e.g. 7-bit), whose output controls the HV output stage 84.

For impedance measurement/characterization module 58, 12 out of 40 Demux inputs 64 are selectively connected to the 16:1 MUX 59 made of HV transistors, allowing 48 electrodes to be characterized. The HV MUX 59 is also connected to the power converter 54 outputs, and two of the MUX inputs 66 are reserved for external sensors such as, but not limited to, inertial and temperature sensors (not shown). In one embodiment, the SoC 15 further supports chip clustering using a 2-bit ID control 68.

Figure 5:
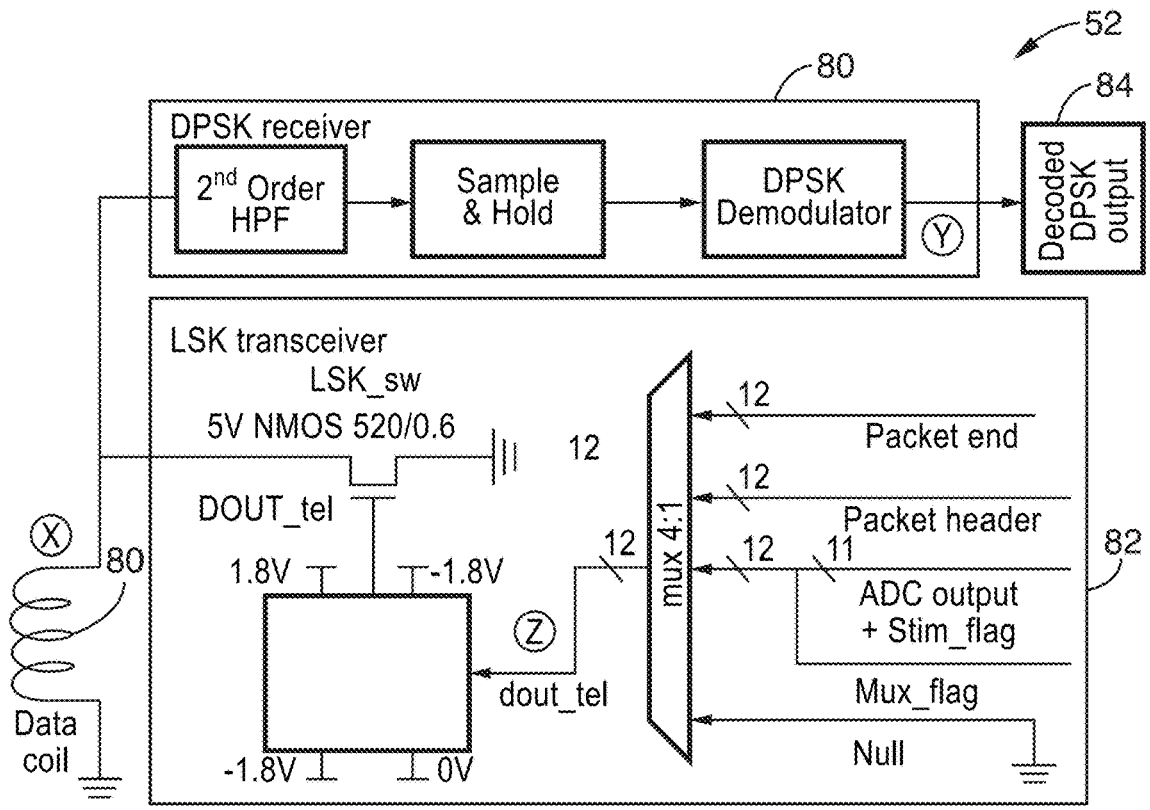
FIG. 5 shows a schematic diagram of a quasi full-duplex transceiver incorporating a DPSK (forward link) and LSK (reverse link) in accordance with the present description.

Stimulation parameters may be stored within stimulation parameter storage 48 and distributed to each stimulation driver 84 through a global data bus/stimulation controller 70. This storage function enables the concurrent stimulation and recording, as it can continuously trigger the stimulation while the recording function is on. In another setting when recording is not required, the stimulation parameters can be real-time adapted after receiving new commands from the DPSK receiver 70 (FIG. 5).

A multi-channel stimulation recording circuit 62 (implemented as a 16-channel recording front-end in FIG. 3A and FIG. 3B) is incorporated on the SoC 15 for receiving input from the array 16 or from other kinds of electrodes/sensors that can be coupled to the SoC 15. For example, stainless steel wire electrodes 36 may be used for EMG recording. In another embodiment, one or more cuff electrodes for nerve stimulation/recording can be coupled to the SoC 15 through a flexible substrate which serves as an interposer (see substrate 200 shown in FIG. 17A through FIG. 17C). Signals from multi-channel stimulation recording circuit 62 and HV Mux 58 are acquired by an analog-to-digital converter (ADC) 56 (e.g. 10-bit) for output to the controller 50. Each recording channel is preferably configured to have its own reference and input. Thus the recording support both 1) bipolar recording 2) common-reference recording by shorting the ref input in each recording channel together.

The first stage of front-end 62 is an AC-coupled amplifier 45 adapted with a targeted gain of 40 dB. The second stage 47 is a programmable bandpass filter composed of an R-C high-pass filter and a gm-C low pass filter. The high-pass and low-pass cutoff frequencies of the subsequent bandpass filter are adjustable by tuning the resistance of the pseudo-resistor via $V_{tune}$ and by altering the transconductance of the gm-C filter with a 1-bit digital control. $V_{tune}$ is pre-set to 1.8 V through an on-chip resistor and can be adjusted by connecting an additional external resistor to the SoC pin. The third stage 49 is a programmable gain amplifier with 2-bit control to tune the ratio of the input and feedback resistors. Subsequently, a 16:1 multiplexer 51 connects 16-channel outputs to the back-end ADC 56 for signal digitization.

The ADC 56 is preferably with a pipelined topology, resolving the rail-to-rail input into a 10-bit digital output. The input rail-to-rail unity gain amplifier (see front end 62) buffers the recorded single-ended signal. A first stage of the ADC 56 (not shown) converts the incoming single-ended signal to pseudo differential outputs. All ADC stages are also designed as differential to improve SNR of the full chain and increase tolerance to common-mode errors. The remaining architecture follows a conventional pipelined ADC topology with a switched-capacitor gain amplifier (not shown) at the core of each stage. An error correction circuit (not shown) may be added to allow corrections for the comparator offset and other non-idealities. This is accomplished by designing each ADC stage in the pipeline to have a 1.5-bit topology, where the 0.5 bit overlaps with the next stage's output to allow for digital error correction The SoC 15 may also be clustered to expand the number of channels. For example, sharing the same coils 18a, 18b, a four-SoC cluster (not shown) may be implemented to provide 640-channel stimulation, 64-channel recording, as well as 192-channel impedance characterization. In such multi SoC configurations, individual SoC's may share/divide functionality. For example, in another configuration, a first SoC (not shown) may be dedicated for high-density multi-channel recording and be linked to a second SoC (not shown) by transmitting its recording output to the LSK transmitter 82 input (FIG. 5). This adds the flexibility and versatility of the proposed SoC.

Figure 4:
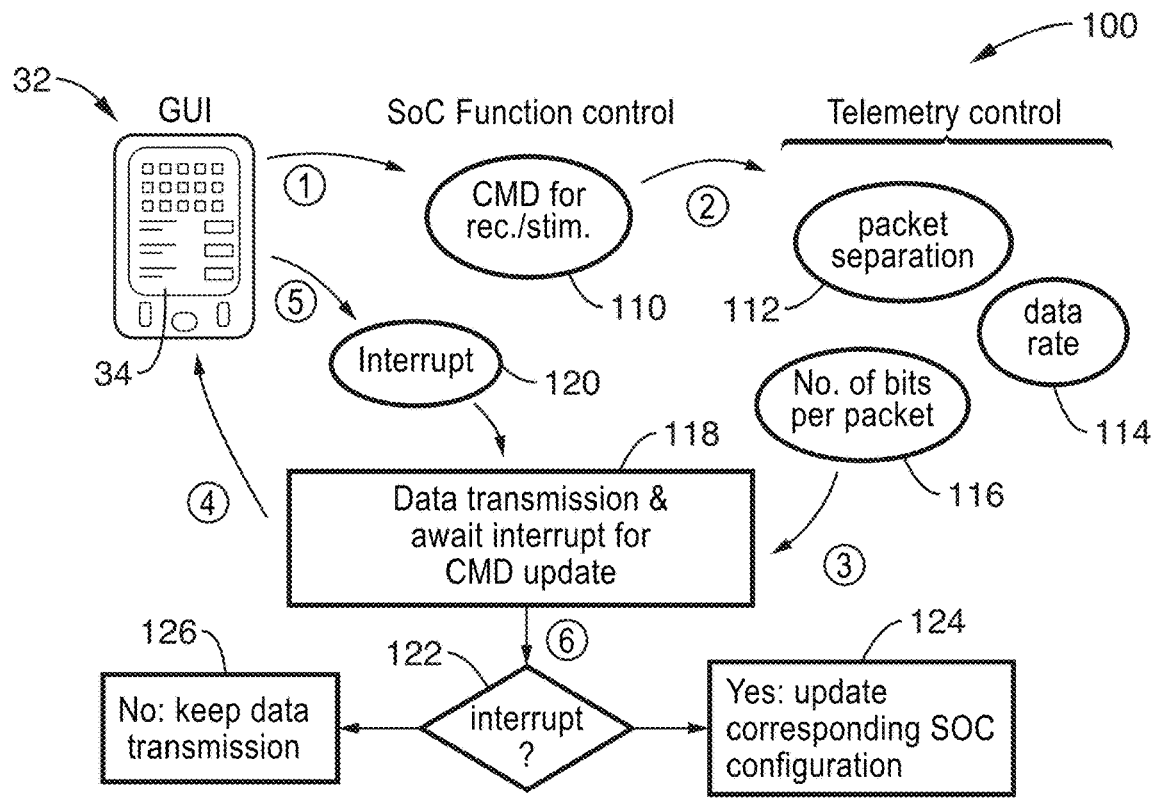
FIG. 4 shows an operation flow and block diagram of data telemetry of the quasi full-duplex data link of the present description.
Figure 6:
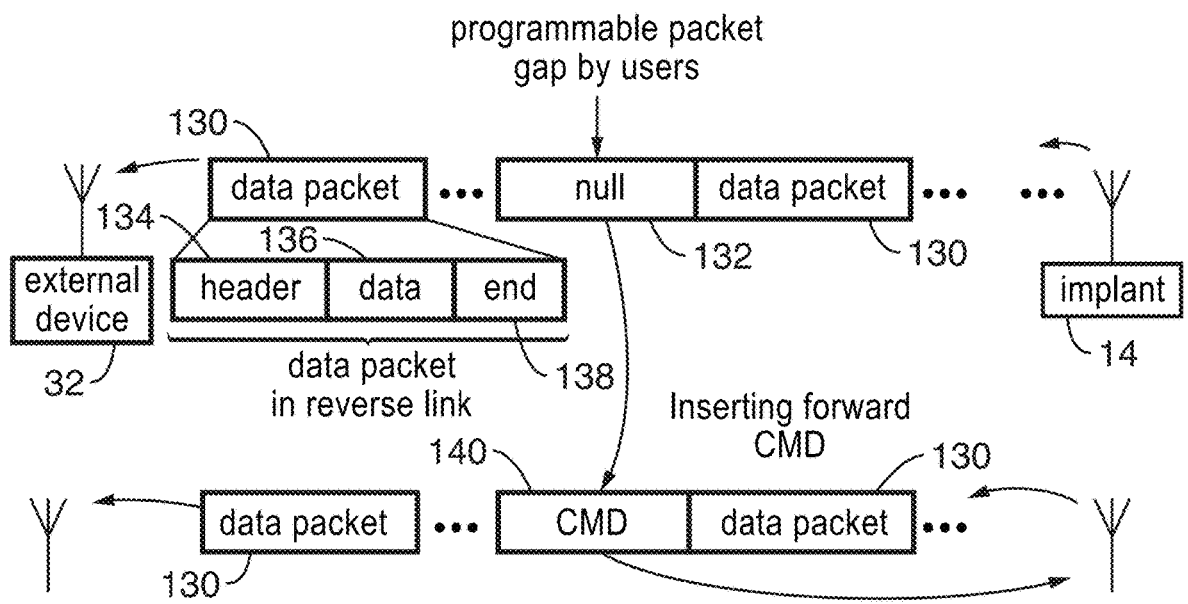
FIG. 6 is a block diagram illustrating a quasi full-duplex mode to support a closed loop system.
Figure 7:
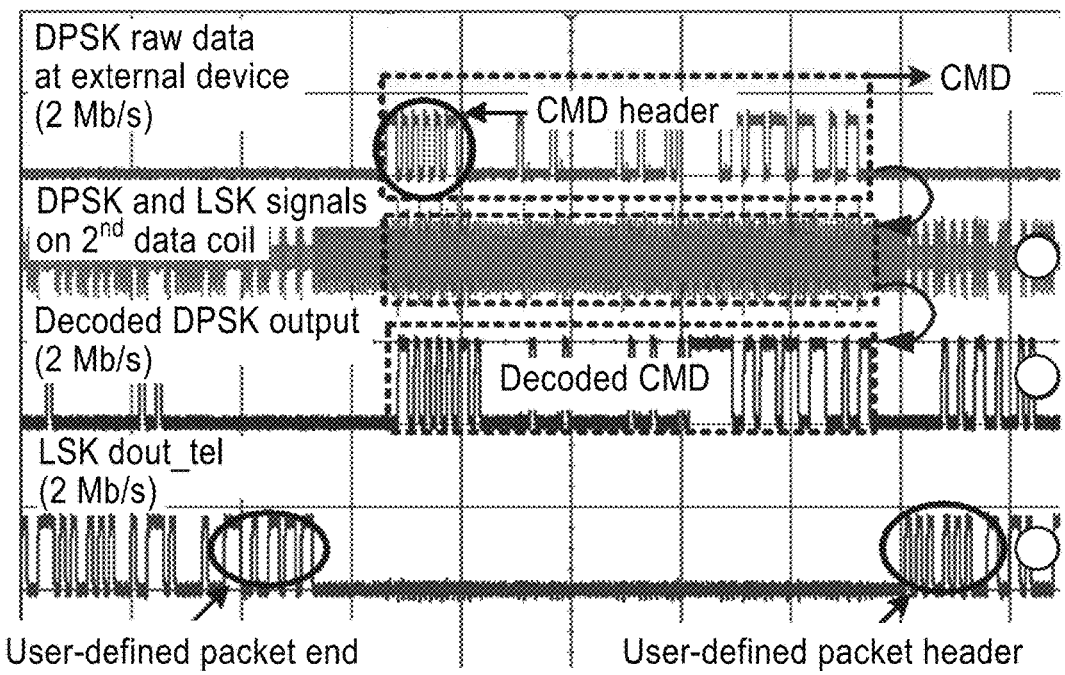
FIG. 7 illustrates the measured bi-directional data link under the quasi full-duplex mode illustrated in FIG. 6.

FIG. 4 through FIG. 7 show the operation of the quasi full-duplex data link and its implementation. FIG. 4 shows an operation flow and block diagram of a data telemetry scheme 100 for a quasi full-duplex data link 100 in accordance with the present description. FIG. 5 shows a schematic diagram of a quasi full-duplex transceiver 52 incorporating a DPSK receiver (forward link) 80 and LSK transceiver 82 (reverse link) in accordance with the present description. FIG. 6 is a block diagram illustrating a quasi full-duplex mode to support a closed loop system. FIG. 7 illustrates the measured bi-directional data link under the quasi full-duplex mode illustrated in FIG. 6.

Referring to the data telemetry scheme 100 of FIG. 4, GUI 34 is configured for execution on external device 32 processor to send out SoC 15 function control commands (CMD 110) for recording/stimulation. Telemetry control is also implemented to send CMD 110 in the form of packet separation 112, data rate 114, number of bits per packet 116, etc. At block 118, data is transmitted back to the external device 32, and the system awaits interrupt 120 (from device 32) for CMD update. At block 122, if interrupt is detected, the corresponding SoC configuration is updated at block 124. Otherwise, data transmission is maintained at block 126.

In one embodiment, a full-duplex bi-directional data link is established through two separate coil pairs (i.e. one high Q coil pair 18a for power transmission and one low-Q coil pair 18b for data transmission). Although the forward command can be sent through the data coil while the reverse data link is built through the power coil, realizing a high data rate reverse link with a power coil is disadvantageous because high wireless power transfer efficiency and high Q-factor requirements limit the data rate. Thus, unlike other approaches using a power coil for data link, the low-Q data coil 18b is used for both the forward and reverse data links to implement the full-duplex bi-directional data transmission. In the forward data link, DPSK-modulated data 84 is transmitted to configure the implant 14. In the data packet 130 format shown in FIG. 6, each packet contains a header 134, digitized data 136, and an end marker 138. The SoC 15 is configured to discard any DPSK output packet without a correct header. Once the rendezvous device 12 recognizes the end marker 138, it can send a CMD 110 to the SoC 15 within the time gap 132 (i.e. programmable packet gap) between data packets 130. The inserted forward command 110 is shown in packet gap 140 in FIG. 6. When recording is not enabled, the forward command can be continuously sent to update the stimulation parameters.

Referring back to FIG. 5, the data transceiver 52 comprises a DPSK receiver 80 for its good immunity to interference and an LSK transmitter/transceiver 82 for low-power consumption (<4 μW). DPSK and LSK modulations were chosen because these two modulation schemes modulate digital data in different domains (i.e. DPSK is in phase, LSK in amplitude). This particularly beneficial because both DPSK and LSK signals on the data coil 18b would be both seen by the DPSK receiver 80 in the SoC 15. Thus, the DPSK and LSK modulations in different domains mitigate interference between receiving and transmitting modes. It is also appreciated that different modulation schemes may be selected and implemented so that the forward and reverse links modulate signals in different domains.

Figure 8:
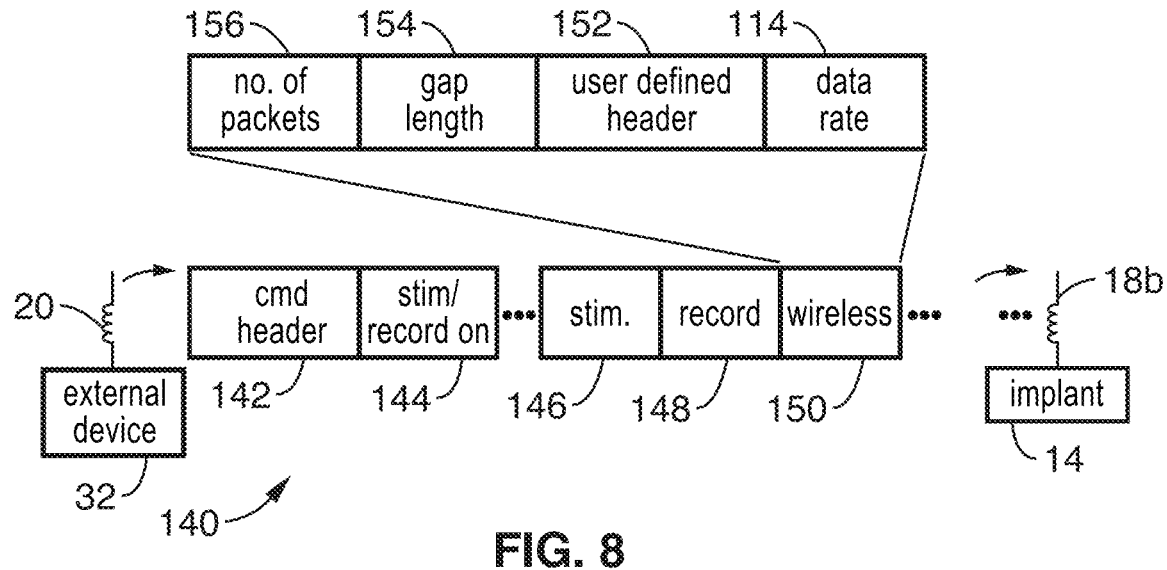
FIG. 8 shows a diagram of the forward data link and corresponding command packet structures

FIG. 8 shows a diagram of the forward data link and corresponding command packet structures. The command 110 includes small packets that contain information for each of each modality supported by the implant 14 (e.g. stimulation parameters 146, recording setup 148, stimulation/ record on 144 impedance measurement, reverse data link, etc.) along with command header 142 and wireless 150 packets. With the exception of the command header 140, the sequence/order of other small command packets can be arranged randomly or be absent if that modality is not used. Notably, once the configuration of the wireless transmission is set, in the reverse telemetry, the SoC 15 transmits the recorded data in packets that has programmable length and is separated by programmable time gaps. Referring to wireless packet 150, the programmable packet length (number of packets 156, defining the length of the recorded data) and gap 132 between packets 130 (defined by gap length 154, see also packet separation 112 in FIG. 4) can be designed and implemented in the forward data link. The programmable packet gap 132 (as defined by gap length 154) between each data packet 130 allows for the insertion of a future forward command 110. Thus, new commands to update the implant configuration can be sent simultaneously at run real time without ceasing the reverse data link or resetting the implant operation. In addition to inserting a gap 132 between each packet 30, the number of recorded data 156 assembled in a data packet is programmable from 1 to $2^{32}$. Once the reverse link is finished, the reverse data transmission from the SoC 15 becomes silent, awaiting a new forward command.

If the LSK transmitter 82 signal happens to have the same pattern of the command header 142, the DPSK receiver 80 might misinterpret it and lead to false electrical stimulation. To avoid the occurrence of the above scenario, two mechanisms are implemented, as illustrated in FIG. 7. First, the intrinsic difference between DPSK and LSK signals is leveraged. The DPSK receiver 80 on the SoC 15 decodes the incoming data by only recognizing the phase shift in the signal on the coil 18b. Thus, the LSK signal would not be decoded by the DPSK receiver 80 as LSK adopts amplitude modulation. One might also choose FSK, but the signal amplitude would vary a lot as the quality factor on the coil varies with frequency. On the other hand, DPSK can also be used for reverse link, but a switch between transmitter 82 and receiver 80 must be used to avoid direct coupling from transmitter to receiver. Second, a command header 142 check was implemented in the DPSK receiver 80 on the SoC 15. The header check differentiates the command packet 140 from all other noise appearing on the data coil 18b. The error bit due to the LSK signal on the coil will thus be discarded, as it does not pass header check. This methodology allows the carrier frequency of the forward and reverse telemetry to be identical, and simplifies the coil 18b configuration in that it only needs to be optimized at one single frequency for the data link. Furthermore, a transmitter/receiver duplexer switch is not required, lowering hardware cost. Test results (see FIG. 15) show both forward DPSK and reverse LSK signals can co-exist on the same coil without contention. The LSK signal may result in error bits at the DPSK-demodulated output, but they fail the CMD header check and are discarded.

One feature of the system 10 of the present description is characterization of the impedance of the electrode-tissue interface to ensure no violation on both the compliance voltage of the stimulator and the water window of the electrode. While characterizing bio-impedance across a broad spectrum generally involves sophisticated equipment and time-consuming processes, doing so at a fixed frequency provides limited information. Some conventional methods calculate only the impedance at a specific frequency by injecting a small sinusoidal signal. Electrochemical impedance spectroscopy (EIS) also has been widely used to obtain the electrode-electrolyte impedance at a wide spectrum, but it is challenging to embed this system into an implant. Furthermore, the level of inaccuracy increases because EIS is based on the analysis of small sinusoidal signal characterization while a square wave stimulus with larger intensity is used for stimulation.

Figure 9:
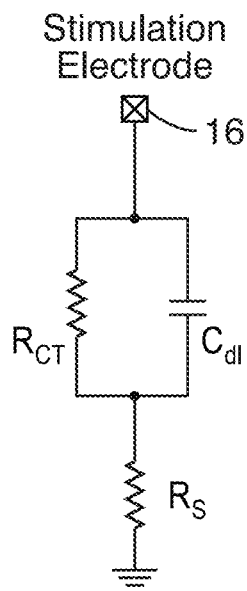
FIG. 9 shows a schematic circuit diagram for a Randles cell circuit model.
Figure 10:
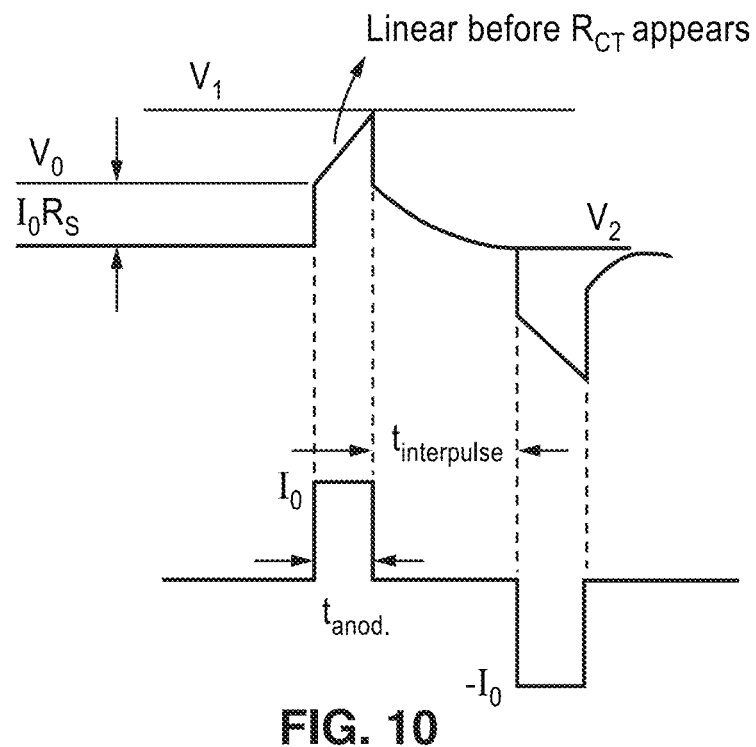
FIG. 10 is a plot illustrating electrode potential resulting from a biphase stimulus with small intensity and inter-pulse delay.
Figure 11:
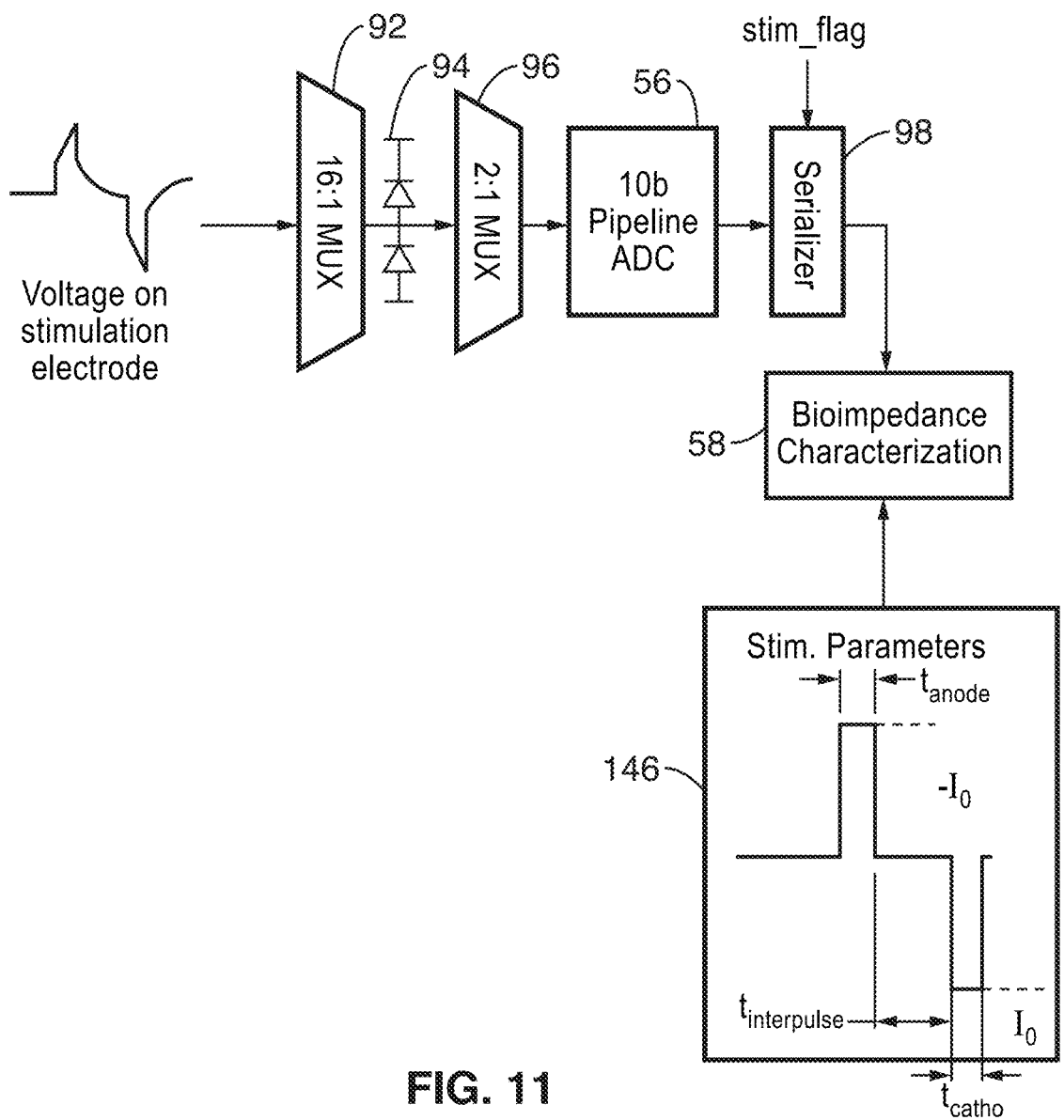
FIG. 11 is a diagram of the circuit implementation for bio-impedance characterization in accordance with the system of the present description.

FIG. 9 through FIG. 14 illustrate a hardware-efficient time-domain method to for in-situ bio-impedance characterization in accordance with the system 10 of the present description. The system 10 of the present description is configured to receive bio-impedance data via fixed frequency, and also the Randle cell model electrode model. An exemplary Randles cell circuit model of the electrode-tissue interface is shown in FIG. 9, wherein $R_s$ represents tissue resistance, $R_{CT}$ represents charge transmission resistance, and $C_{dl}$ represents the double layer capacitance. FIG. 11 shows a flow diagram of an implementation for bio-impedance characterization using the components of the SoC 15 in accordance with the system 10 of the present description.

After stimulation parameters 146 (FIG. 8) are decoded by SoC 15, the parameters are first stored in its on-chip registers (stimulation parameters storage 48, see FIG. 3). The parameters 146 may include, but are not limited to: channels to be activated, stimulation intensity, pulse width, polarity, inter-pulse delay, location, etc., and are distributed to each stimulation driver through a global data bus/stimulation controller 70. When there is stimulation, the Stim_flag bit is set to bit 1 to trigger stimulation, incorporating the stored parameters.

Subsequently, a biphasic, low-intensity current stimulus with inter-pulse delay is applied to an electrode 16. FIG. 10 shows a plot illustrating electrode potential resulting from a biphase stimulus with small intensity and inter-pulse delay. By measuring the electrode over potentials $V_0$, $V_1$, and $V_2$, tissue resistance ($R_S$), double layer capacitance ($C_{dl}$), and charge transfer resistance ($R_{CT}$) are accordingly derived according to Eq. 1, Eq. 2 and Eq. 3:

$$R_S = V_0/I_0,$$ Eq. 1

$$C_{dl} = (I_0 \times t_{anode})/(V_1 - V_o),$$ Eq. 2

$$R_{CT} = -t_{interpulse}/(C_{dl} \ln(V_2/(V_1 - I_o R_s)))$$ Eq. 3

Low-intensity stimulus ensures $R_{CT}$ does not complicate the $C_{dl}$ computation. Inter-pulse delay provides a passive discharge period for $R_{CT}$ acquisition.

Figure 12:
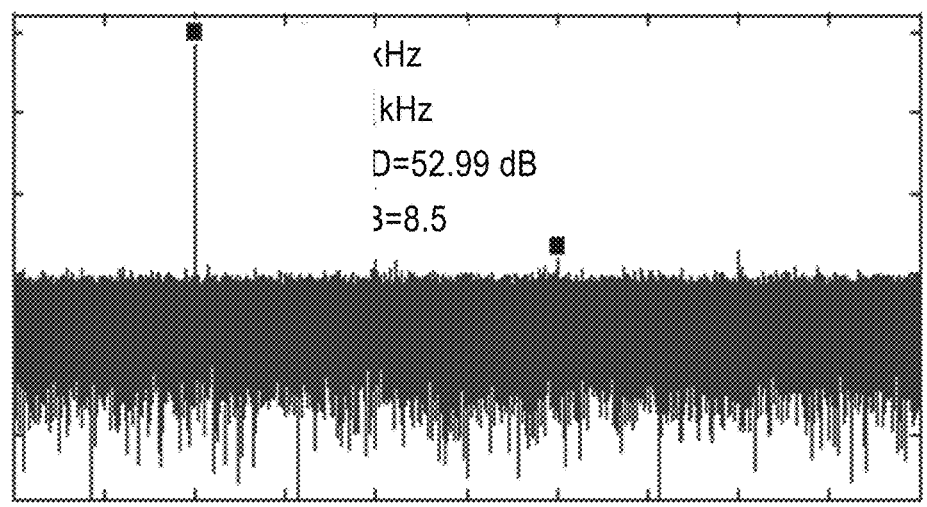
FIG. 12 shows a plot of exemplary ADC output.

In the circuit implementation for bio-impedance characterization is shown in FIG. 11, both recording and impedance characterization circuits share the same ADC 56, whose input voltage is confined by voltage-clamp diodes. FIG. 12 shows a plot of the ADC 56 output. Of the 40 Demux inputs, 12 are connected to a 16:1 multiplexer 92 made of high voltage transistors for impedance characterization. Voltage clamp diodes 94 are cascaded at the 16:1 MUX 92 output to protect the 2:1 multiplexer 96 made of low-voltage transistors. The measured electrode overpotential is digitized by the 10-bit pipeline ADC 56 that is shared with the recording front-end 62.

The same neural stimulator 16 is used for impedance characterization. The Stim_flag bit is inserted into the serialized ADC 56 output to denote the stimulation onset. It is important to know that the onset of stim_flag signifies the position of $V_0$. The serializer 98 then incorporates the Stim_flag bit into the serialized ADC 56 output. Based on the previously described method, the bio-impedance characterization module 58 then estimates the Randles cell electrode model with the known stimulation parameters and measured electrode overpotential, i.e. the impedance characterization module 58 searches for $V_0$, $V_1$, and $V_2$ based on the Stim_flag bit and the given stimulation parameters 146.

Figure 13:
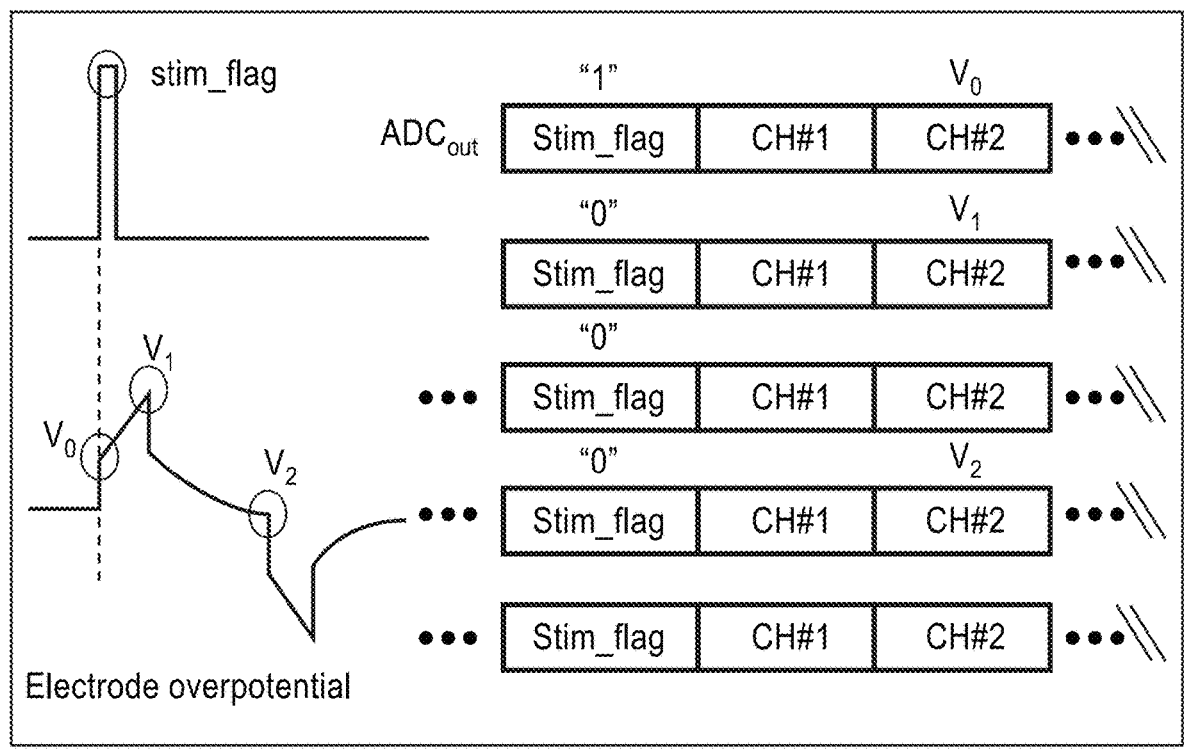
FIG. 13 shows a schematic diagram of bio-impedance characterization with respect to Stim_flag and the electrode over potential.

FIG. 13 shows a schematic diagram of bio-impedance characterization with respect to Stim_flag and the electrode over potential. Stim_flag is periodically inserted before the first specified channel is digitized (e.g. CH #1). If Stim_flag=1, $V_0$ can be identified. $V_1$ and $V_2$ are then found via the stored pulse width and inter-pulse delay.

Using the characterization of electrode #2 (CH #2) as an example, when Stim_flag is triggered to "1" to indicate the onset of a stimulus, the measured electrode overpotential following Stim_flag is indicated as $V_0$. As the stimulation parameters, such as intensity ($I_0$), pulse width ($t_{anode}$ and $t_{cathod}$), and interpulse delay ($t_{interpuls}$e), are stored in the SoC 15 using an appropriate data structure developed in, V1 and V2 can be found accordingly after the Stim_flag bit is raised to high. It is important to note that in using the proposed method, only three values of the electrode voltage are required to estimate the impedance. Moreover, instead of designing complex or specific circuits for impedance measurement, we take advantage of the intrinsic functions supported by the SoC 15 (i.e. recording and stimulation), that allow the derivation of the equivalent circuits model of the electrode-electrolyte interface.

Figure 14:
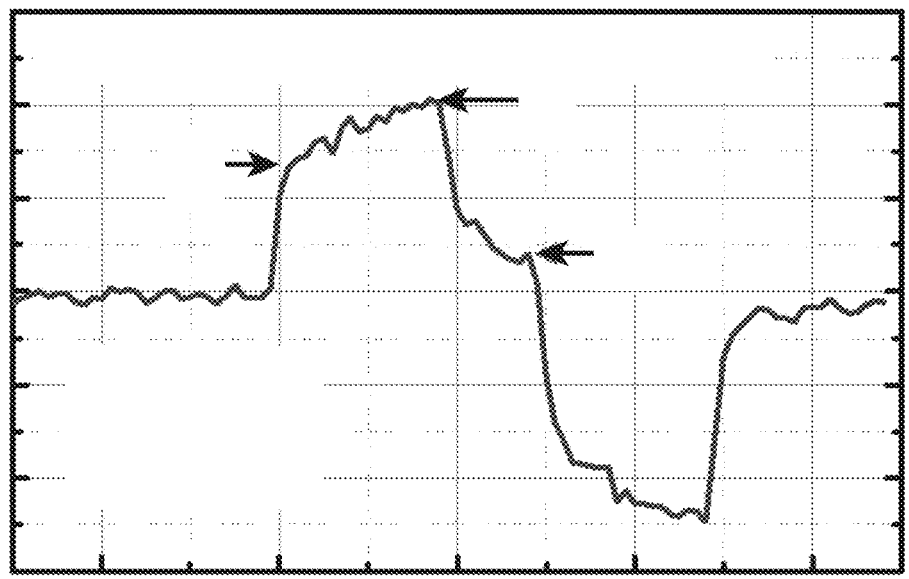
FIG. 14 is a plot of recorded in situ electrode over potential from a paralyzed rat specimen.

FIG. 14 is a plot of recorded in situ electrode over potential from a paralyzed rat specimen.

Figure 15:
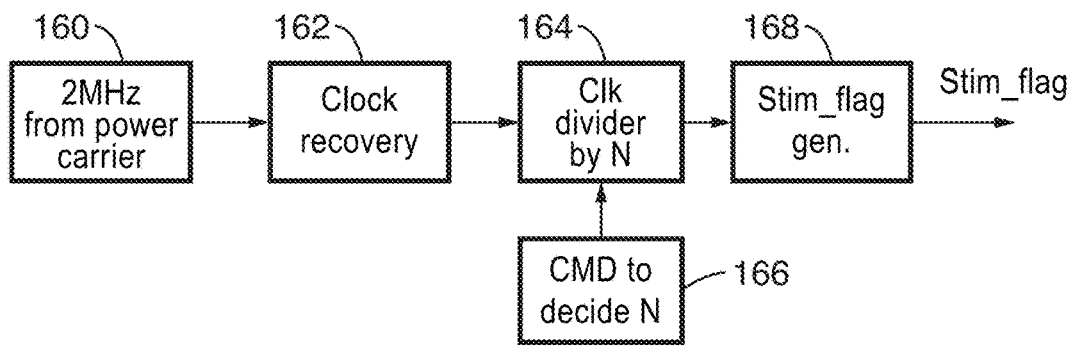
FIG. 15 shows a schematic circuit diagram of the circuits to generate Stim_flag.

To reduce the data rate during reverse telemetry, a mode to selectively transmit only the measured values of $V_0$, $V_1$, and $V_2$ is supported. FIG. 15 shows a schematic circuit diagram of the circuits to generate Stim_flag. The power signal 160 is used to recover the 2 MHz clock at 162. The user command 166 is then input to clock divider 164, the output of which is then processed by Stim_flag generator 168 to produce Stim_flag according to the user command 166.

Simultaneous recording and stimulation are important features of the implant 14 of the present description. One prominent example is a closed-loop deep brain stimulator that performs stimulation only when abnormal brain activity is sensed. However, a different scenario exists for an implant 14 for the system 10 for motor function recovery as detailed in FIG. 1, which uses continuous stimulation along with recording, and synchronizes wireless transmitted recorded data with stimulation onset to allow physicians/scientists to investigate the causality between stimulation and recording. It should be noted that the process used for a commercial physiological stimulation/recording system to sync the recording and stimulation (wherein the stimulation and recording are performed with the same controller (i.e., PC, laptop, FPGA) that talks to both functional blocks directly and knows the operation timing of both functions) is a very different and simplified operation than for an implantable device. When stimulation parameters are loaded to an implant by the clinician, there is no way to exactly identify the stimulation onset. Moreover, this synchronization is useful in impedance characterization as it indicates which portion of the recorded signal should be used for impedance characterization.

Figure 16:
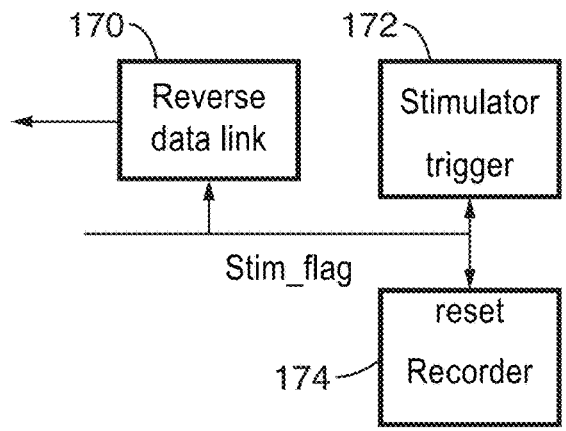
FIG. 16 shows a diagram of the Stim_flag bit used for onset timing of stimulus firing encoded into the recorded data to be and enabling the wireless data synchronization over a reverse data link.

As shown in FIG. 16, by leveraging the Stim_flag bit, the onset timing of stimulus firing is encoded into the recorded data to be transmitted (e.g. for stimulator trigger 172), enabling the wireless data synchronization over reverse data link 170 with what is happening in the implant 14. On the other hand, the Stim_flag bit can be selectively connected to reset the recording circuits 174 as the recording circuits might be saturated due to the large stimulation artifact (amplifier saturation largely depends on the separation between stimulation and recording electrodes). Resetting the recording circuits during the stimulation onset expedites its back-to-normal-function time.

Figure 17A:
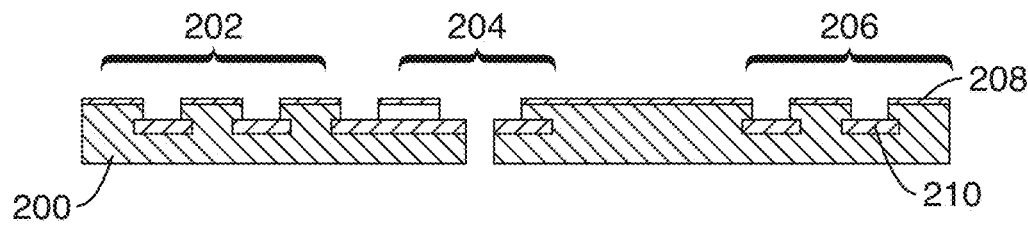
FIG. 17A through FIG. 17C show thin film polymer packaging of the implant though various process phases.
Figure 17B:
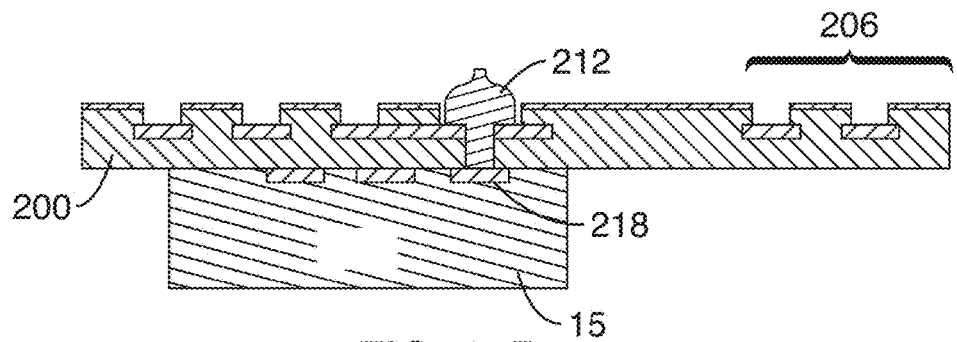
Figure 17C:
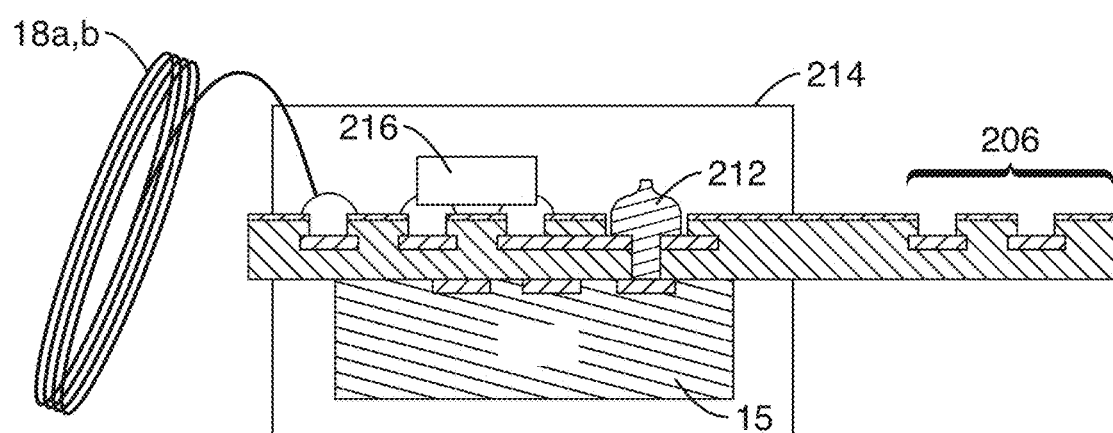

FIG. 17A through FIG. 17C show thin film polymer packaging of the implant comprising a bump pad design though various process phases.

As shown in FIG. 17A, a metal trace 210 (e.g. Pt/Ti layer having a thickness between 200 nm and 10 nm) can be built on a polymer substrate 200 (e.g. polyamide layer having a thickness of 8 µm) having a CMOS top layer 208 (e.g. 120 nm thick SiO2). Substrate 200 may be configured with both soldering pads 202 for circuit assembly and electrodes 206 for neural electrode array 16 such that the SoC 15 and neural electrode array 16 are integrated on the same substrate 200. The polyimide substrate can have two different kinds of pads: 1) solid pads 202, which are used to integrate the passive components directly onto the substrate 200 by soldering, and 2) bump pads 204 with a through hole in the center, which are used for integrating the chips or circuit die beneath the substrate.

As shown in FIG. 17B, a metal (e.g. gold, aluminum, etc.) bump 212 may then be coupled to connect chips or circuit (e.g. connects 218 of SoC 15) to the metal trace 210 on the polyimide substrate 200 directly. A plurality of bumps 212 can be placed on one bump pad to strengthen the connection of the SoC 15 and the flexible substrate 200. In a preferred embodiment, the size of the bump pads 206 and corresponding through hole is smaller than the pad of the SoC 15.

Referring to FIG. 17C, coils 18A, 18B, passive components 216 (e.g. 0201-SMD capacitors), wire electrodes, etc. may then be soldered on to pads 202, and SoC 15 and passive components 216 encapsulated in biocompatible epoxy 214. Discrete components may be soldered or adhered to the flexible substrate through conductive epoxy to minimize device footprint. Bonding wire may be used in conjunction with the metal trace 210 on the flexible substrate 200 for connecting two different pads 202 or components 216.

In a preferred embodiment, the biocompatible epoxy 214 has a similar coefficient of thermal expansion (CTE) to that of the silicon-based SoC 15 and the polyimide substrate 200.

Multiple SoC's 15 can be integrated on the same flexible substrate 200 to expend the number of stimulation and recording channels. A first SoC can also be integrated with another SoC dedicated for high-density recording by connecting the recording output to the LSK transmitter input of the SoC. Also, multiple stimulator outputs can be combined/grouped through the metal connection on the flexible substrate 200 to increase the stimulation intensity.

In one embodiment, the thickness of the flexible substrate is 8 µm, and can range from 8 µm-20 µm to tune its flexibility for different applications.

By utilizing this integrated design, the additional space generally used for the wire of wire bonding is no longer needed (zero distance from pads on the substrate to the pads of the chips or circuit die). Therefore, the entire form factor of the packaging can be greatly reduced. Furthermore, the electrode array 16 is embedded into the polyimide substrate 200, easing the packaging/assembling process.

Figure 23:
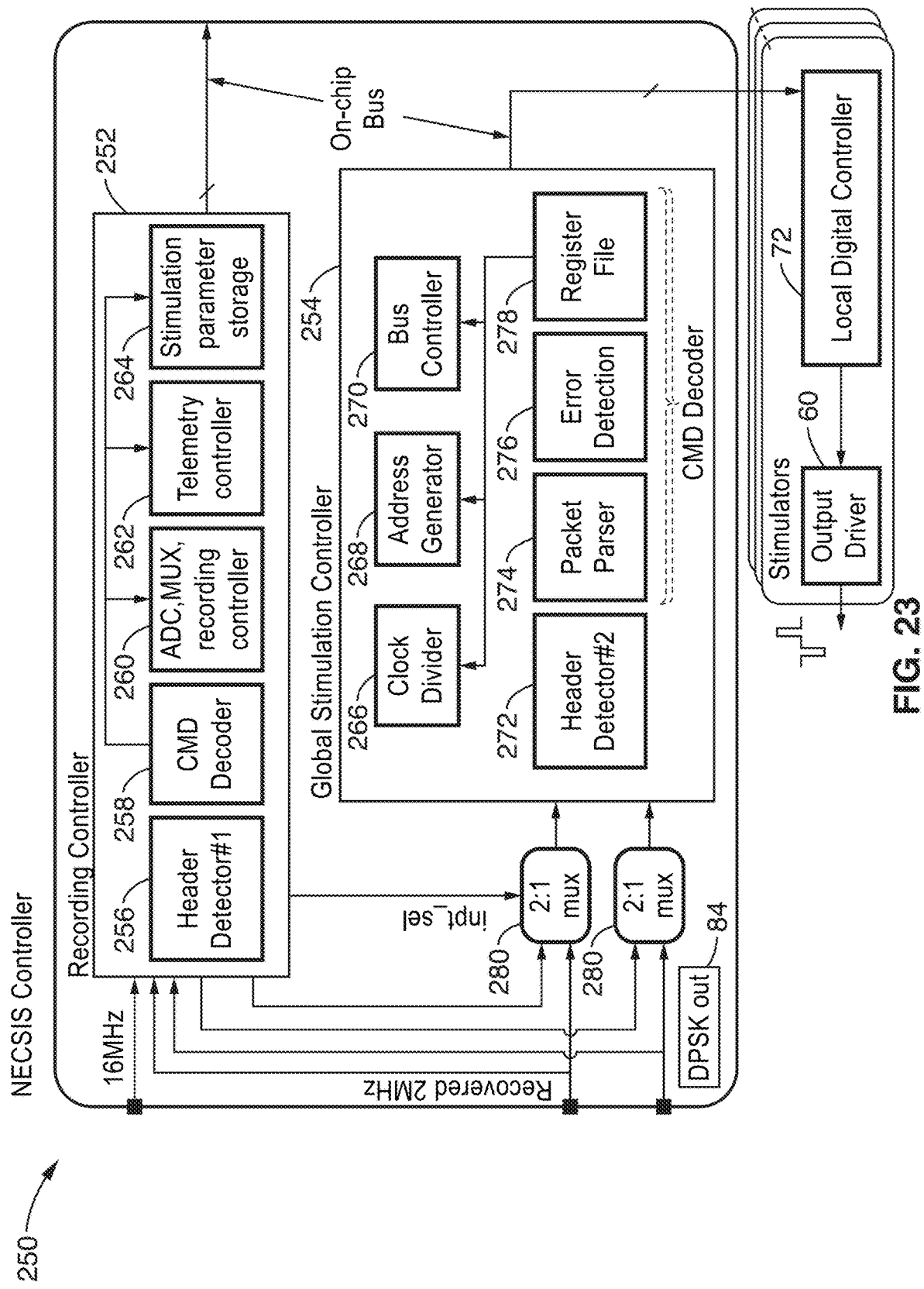
FIG. 23 shows a schematic diagram of an alternative controller in accordance with the present description.

FIG. 23 shows a schematic diagram of an alternative NECSIS controller 250 that may be implemented with SoC 15. The controller 250 primarily comprises a global stimulation controller 254 and a recording controller 252. The incoming DPSK signal (e.g. DPSK out 84 (FIG. 5)) contains a corresponding header and command, wrapped in a packet to control either the stimulation or recording functions. During the default operation of the NECSIS controller 250, the stimulation and recording controllers 254/252 both listen to the incoming DPSK output 84, but only react to the command that can pass its own header check. Header Detector #1 (256) and #2 (272) will first examine the DPSK data input to determine whether the incoming data has the header it requires. If not, it will discard the data.

When the implant 14 is intended for stimulation, the DPSK output containing header #2 will be recognized at header detector #2 272 and decoded by the global stimulation controller 254 and will be distributed to the local digital controller 72 of each output driver 60 for stimulation control. Header detector 272 first recognizes the command. The packet parser 274 and error detection 276 modules then analyze and recover the command if there are bit errors. Then the command will be written into multiple registers (e.g., D-flip-flop). Subsequently, based on the information stored, the registers file module 278 relays the command to the 1) clock divider 266 controlling the system clock, 2) address generator 268 controlling which and how many channels may be stimulated, and bus controller 270 that distributes the command to each local controller 42. Subsequently, similar to the Ethernet, every local controller 72 is assigned a unique address, and each set of stimulation parameters running on the bus comes with an address. Local controllers 72 catch the parameters from the bus when two addresses match and apply the received commands to drive the corresponding output driver 60. This allows the stimulation parameters of intensity, stimulus polarity, pulse width, and interpulse delay to be independently programmed in each channel.

On the other hand, when the implant 14 is intended for recording or performing simultaneous recording and stimulation, the recording controller 252 takes over the control of the SoC once it recognizes the DPSK output signal 84 containing header #1. When Header Detector #1 256 recognizes the command, the CMD Decoder 258 decodes the command, which are then distributed to 1) ADC, Multiplexer (MUX), recording circuits 260 to determine the gain, bandwidth, channels of interests, and ADC sampling frequency, 2) the telemetry controller 262 to select/determine the data rate, the size of packet to be transmitted, and the length of the packet gap, and 3) the stimulation parameter storage 264 that can be used to configure the stimulation parameters for each channel.

Moreover, in order to perform simultaneous recording and stimulation, the recording controller 252 sets a 2:1 Multiplexer (MUX) 280 so the global stimulation controller 254 only takes commands from the recording controller 252. The stored stimulation parameters 264 are relayed to the global stimulation controller 254 to enable concurrent stimulation and recording.

It is appreciated that recording circuitry can be configured in both bipolar recording or common reference recording mode. Furthermore, both the compliance voltage of the stimulator and the supply voltage of the digital controller are monitored and used as feedback signal for closed-loop power telemetry.

Example 1

FIG. 18A through FIG. 22 illustrate an experiment testing an exemplary prototype of system of the present description on a paralyzed rat. The prototype incorporated a SoC 15 implemented in HV 0.18 µm CMOS with an area of 5.7×4.4 mm². The prototype integrated 172 epidural electrodes, four EMG wire electrodes, two coils, six 0201-SMD capacitors, and the SoC into a 0.7 g, 0.5 cm³ package.

Figure 18A:
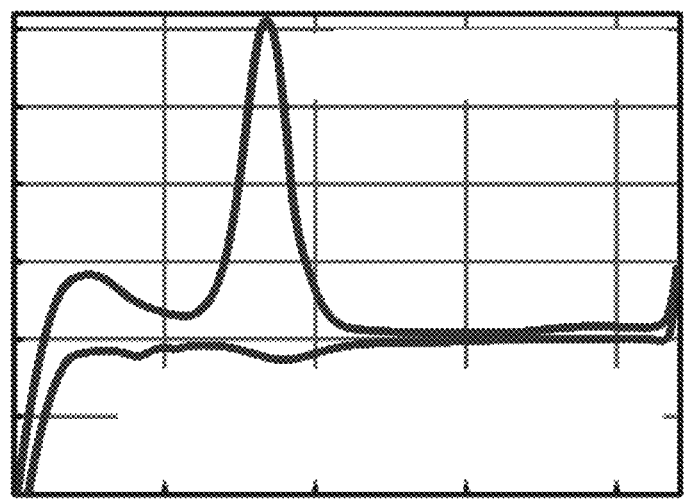
FIG. 18A and FIG. 18B are plots illustrating electrode characterization with respect to cycle voltammetry and stability, respectively.
Figure 18B:
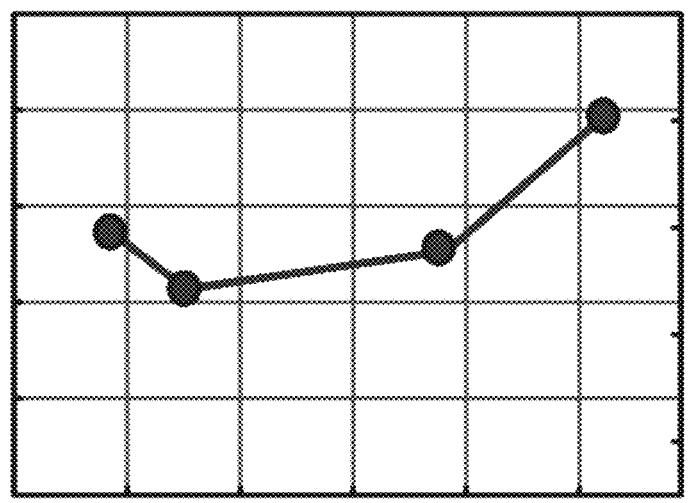

FIG. 18A and FIG. 18B are plots illustrating electrode characterization with respect to cycle voltammetry and stability, respectively. Cyclic voltammetry characterization shows the fabricated epidural electrode has a charge storage capacity of 6.74 µC. The electrode in-vivo test results demonstrate <1.5 kΩ impedance standard deviations during the 52-day post-surgery period.

Figure 19:
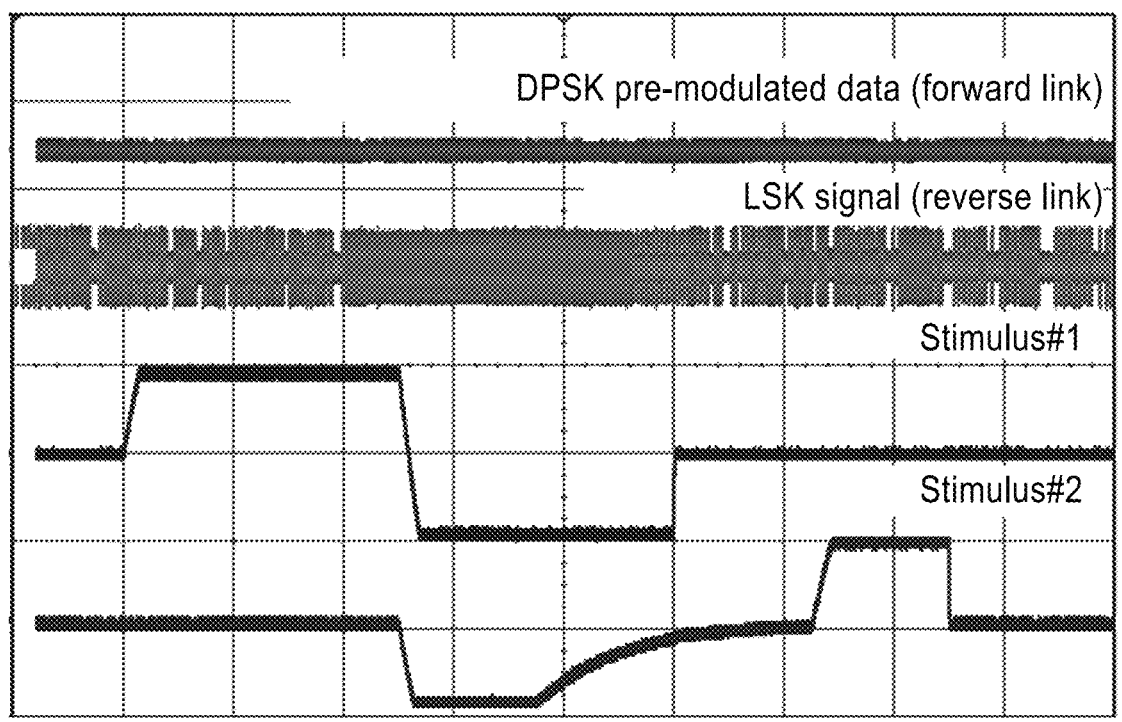
FIG. 19 shows a plot of simultaneous stimulation recording data telemetry.

FIG. 19 shows a plot of simultaneous stimulation recording data telemetry. The LSK data rate was set to 0.5 Mb/s for illustration purposes. Stimulus #1 was anodic first, 0.25 mA, 0.25 ms pulse width (40 kΩ load resistor). Stimulus #2 was cathodic first, 0.25 mA, 0.1 ms pulse width 0.25 ms inter-pulse delay, 0.25 ms starting delay (40 kΩ resistor+2.5 nF capacitor load). No updating CMD was issued and grounding switch was enabled after stimulation.

Figure 20:
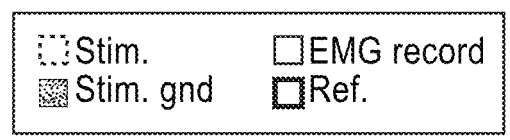
FIG. 20 shows a diagram of the experimental setup for experiments in accordance with the present description.
Figure 20:
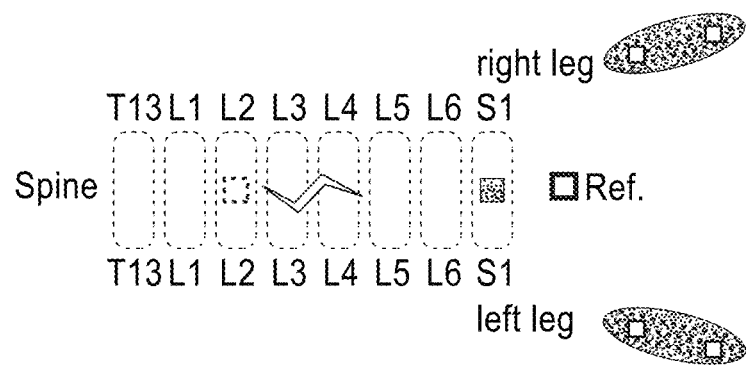

FIG. 20 shows a diagram of the experimental setup for experiments in accordance with the present description.

Figure 21:
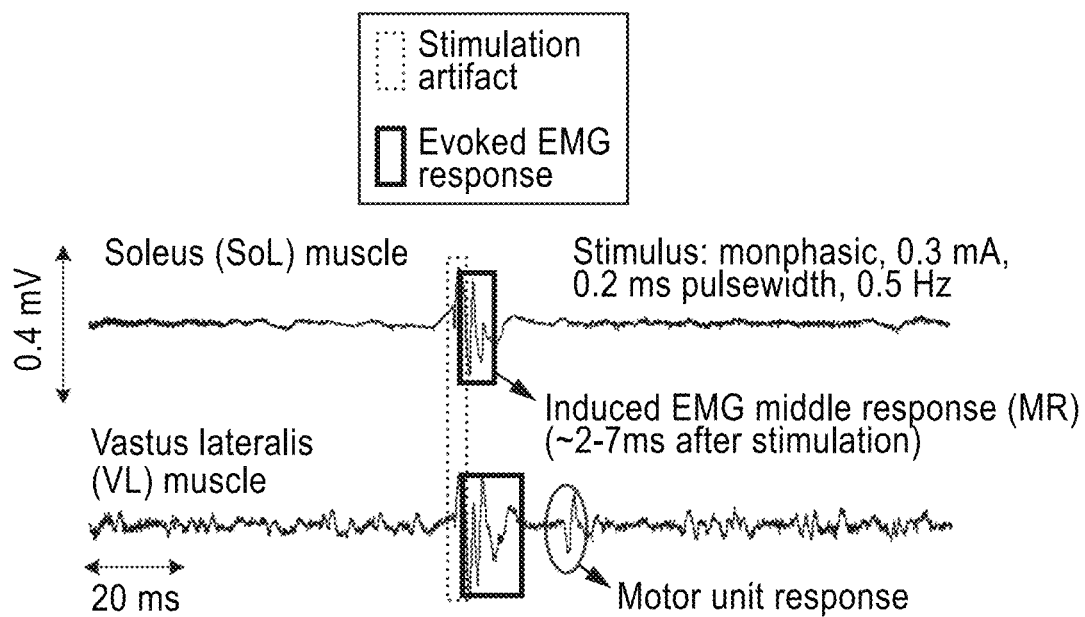
FIG. 21 shows a plot of selected EMG responses from a normal test subject.
Figure 22:
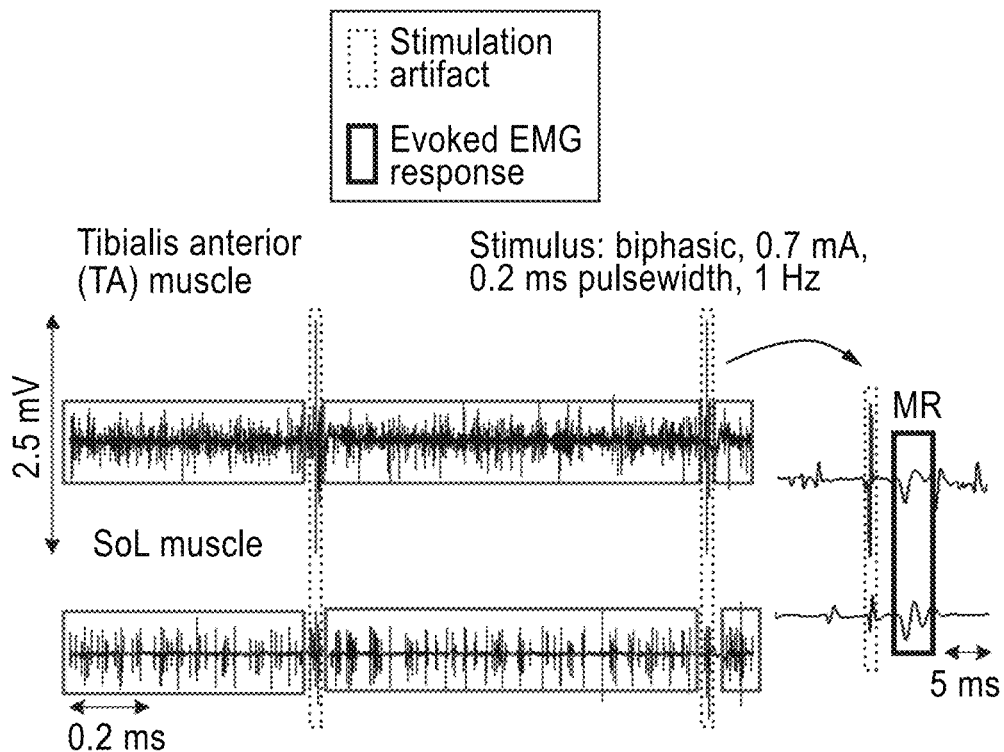
FIG. 22 shows a plot of selected EMG responses from a paralyzed test subject.

FIG. 21 shows a plot of selected in-vivo EMG recordings when stimulating the lumbosacral region of the spine from a normal test subject. FIG. 22 shows a plot of selected in-vivo EMG recordings when stimulating the lumbosacral region of the spine from a paralyzed test subject. Stimulation-induced EMG middle responses and spontaneous onset of motor unit are observed in the leg muscles of the normal rat. Stimulating the paralyzed rat results in consistent EMG patterns required for standing. A stronger stimulation current is applied on the paralyzed rat as its brain-spinal network is injured.

While the embodiments above are directed primarily to technology for motor function recovery after spinal cord injury, it is appreciated the systems and method disclosed above may be implemented for use in a variety of medical applications, such as, but not limited to, retinal prostheses, gastrointestinal implant, vagus nerve stimulation, cortical neuromodulation, or use with stroke patients.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. An implantable stimulator system, comprising: (a) an implantable stimulator circuit configured for implanting within an organism: (b) an external circuit configured for retention sufficiently proximal said implantable stimulator circuit for communicating power to said implantable stimulator circuit, and data to and/or from said implantable stimulator circuit; (c) wherein said implantable stimulator circuit comprises: (i) a first inductive coil configured for receiving power from the external circuit as a power coupling; (ii) a second inductive coil configured for communicating data with the external circuit as a data coupling; (iii) a data link circuit configured for communicating data through said data coupling; (iv) a flexible epidural electrode array comprising a plurality of electrodes; (v) a multi-channel stimulation circuit having a high voltage output stage configured for multiplexed driving of the plurality of electrodes in said epidural electrode array; (vi) a bio-impedance characterization circuit configured for determining bio-impedance at the plurality of electrodes; (vii) a multi-channel stimulation recording circuit; and (viii) a controller circuit and memory configured for storing stimulation parameters and recorded stimulation data, and for controlling stimulation of the plurality of electrodes and communication with the external circuit.

2. The system of any preceding embodiment, wherein said external circuit comprises: at least one inductive coil configured for transmitting power as a power coupling to said implantable stimulator circuit and for communicating data as a data coupling with said implantable stimulator circuit; a data link circuit configured for communicating data through said data coupling; and a controller circuit and memory configured for controlling stimulation in said implantable stimulator circuit and for receiving information transmitted by said implantable stimulator circuit.

3. The system of any preceding embodiment, wherein said implantable stimulator circuit is configured for performing simultaneous stimulation and recording.

4. The system any of the preceding embodiments, wherein said implantable stimulator circuit is configured for performing real time adjustment of stimulation parameters used for providing stimulation of a target treatment region.

5. The system of any preceding embodiment, wherein said controller circuit, bio-impedance characterization circuit, multi-channel stimulation circuit, data link circuit, and multi-channel stimulation recording circuit of said implantable stimulator circuit are integrated as a system on chip (SoC).

6. The system of claim 5, wherein said flexible epidural electrode array is integrated with the SoC on a singular flexible substrate.

7. The system of any preceding embodiment, the external circuit further comprising a wireless communications link configured to communicate with a remote user control device.

8. The system of any preceding embodiment, the system further comprising application software for installation on said remote user control device, the application software comprising a user interface allowing a user to send stimulation commands and monitor stimulation information from said external stimulation circuit.

9. The system of any preceding embodiment, wherein implantable stimulator circuit provides one or more of: 160 channels of neural stimulation; 16 channel recording of neural stimulation; and 48 channels of impedance characterization.

10. The system of any preceding embodiment, further comprising a plurality of EMG electrodes at specific locations to provide feedback with respect to stimulation of a target treatment region.

11. The system of any preceding embodiment: wherein the implantable stimulator circuit is configured for placement adjacent or near an injured spinal segment; and wherein the stimulation parameters are configured to promote motor function recovery after spinal cord injury via epidural electrical stimulation of neurons within the target treatment region to reengage a neural network connecting the brain and spinal cord.

12. The system of any preceding embodiment: wherein the implantable stimulator circuit is configured for placement as a retinal prostheses or gastrointestinal implant.

13. The system of any preceding embodiment: wherein the implantable stimulator circuit is configured for placement in the body for vagus nerve stimulation or cortical neuromodulation.

14. An implantable epidural spinal stimulator apparatus for motor function recovery, comprising: (a) an implantable stimulator circuit configured for coupling to a neural network of an organism; (b) a first inductive coil coupled to the implantable stimulator circuit for receiving power as a power coupling within said implantable stimulator circuit, the first inductive coil configured for receiving power from an external stimulator device; (c) a second inductive coil coupled to the implantable stimulator circuit for communicating data as a data coupling with the external stimulator device; and (d) a flexible epidural electrode array coupled to the implantable stimulator circuit comprising a plurality of electrodes; (e) wherein said implantable stimulator circuit comprises a controller, memory and application software stored in said memory along with one or more stimulation parameters for: (i) generating one or more electrical pulses for epidural electrical stimulation of inter-neurons within the target treatment region to reengage a neural network connecting the brain and spinal cord.

15. The apparatus of any preceding embodiment, the implantable stimulator circuit further configured for: (ii) receiving bio-impedance data of the target treatment region via the electrode array; and iii) performing real time adjustment of the stimulation parameters as a function of the acquired bio-impedance data or recorded physiological signals.

16. The apparatus of any preceding embodiment, wherein the implantable stimulator circuit further comprises a data link circuit configured for communicating data through said data coupling with the external stimulator device.

17. The apparatus of an of the preceding embodiments, wherein the implantable stimulator circuit further comprises a multi-channel stimulation circuit having a high voltage output stage configured for multiplexed driving of the electrodes in said epidural electrode array.

18. The apparatus of any preceding embodiment, wherein the implantable stimulator circuit further comprises a bio-impedance characterization circuit configured for determining bio-impedance at the electrodes of said epidural electrode array.

19. The apparatus of any preceding embodiment, wherein the implantable stimulator circuit further comprises a multi-channel stimulation recording circuit for acquiring said bio-impedance data.

20. The apparatus any of the preceding embodiments, wherein said implantable stimulator circuit is configured for performing simultaneous stimulation and recording of acquired bio-impedance data.

21. The apparatus of any preceding embodiment, wherein said implantable stimulator circuit is configured for performing real time adjustment of stimulation parameters used for providing stimulation of a target treatment region.

22. The apparatus of any preceding embodiment, wherein said controller circuit, bio-impedance characterization circuit, multi-channel stimulation circuit, data link circuit, and multi-channel stimulation recording circuit of said implantable stimulator circuit are integrated as a system on chip (SoC).

23. The apparatus of any preceding embodiment, wherein said flexible epidural electrode array is integrated with the SoC on a singular flexible substrate.

24. The apparatus of any preceding embodiment, wherein the data link circuit comprises a bi-directional data link that adopts DPSK and LSK for forward and reverse data link, respectively.

25. A method of performing epidural spinal stimulation for motor function recovery, comprising: positioning an implantable stimulator circuit having an electrode array configured for coupling to a neural network of a target treatment region of the spine; positioning an external circuit at a location of the skin in proximity of the implantable stimulator circuit; providing power transmission from the external circuit to the implantable stimulator circuit via an inductive coupling between the external circuit and the implantable stimulator circuit; providing data transmission between the external circuit and the implanted stimulator circuit via the inductive coupling; generating multi-channel stimulation from the electrode array of said implanted stimulator circuit at the target treatment region; acquiring bio-impedance data from the electrode array at the target treatment region; and performing bio-impedance characterization of bio-impedance at the electrode array or an electrode used for sensing, wherein said bio-impedance characteristics are utilized for controlling the stimulation applied at said electrode array according to one or more stimulation parameters that may be adjusted in real time.

26. The method of any preceding embodiment, wherein power transmission from the external circuit is performed as a power coupling via a first inductive coil coupled to the implantable stimulator circuit and data transmission between the external circuit and the implantable stimulator circuit is performed as a data coupling via a second inductive coil coupled to the implantable stimulator circuit.

27. The method of any preceding embodiment, wherein generating multi-channel stimulation and acquiring bio-impedance data are performed simultaneously on one or more electrodes within the electrode array.

28. The method of any preceding embodiment, wherein generating multi-channel stimulation comprises firing stimuli that are based on the stimulation parameters and triggered by a specified periodic stimulation signal.

29. The method of any preceding embodiment, wherein the stimulation parameters and user specified periodic stimulation signal are pre-configured in the implant.

30. The method of any preceding embodiment, wherein the stimulation parameters and user specified periodic stimulation signal are provided by a user in real-time.

31. The method of any preceding embodiment, further comprising: synchronizing data acquisition and stimulation from the implantable stimulator circuit via wireless transmitted data comprising a recorded physiological signal and stimulation onset information.

32. The method any of the preceding embodiments, further comprising: resetting recording circuitry within the implantable stimulator circuit during stimulation onset by selective connecting of stimulation onset information to reset the recording circuitry.

33. The method of any preceding embodiment, wherein the specified periodic stimulation signal used for triggering data synchronization is also used for impedance characterization.

34. The method of any preceding embodiment, wherein data transmission is provided as a full-duplex data link through a communication protocol that allows user definition of data packet size and gap between each packet within the transmitted data.

35. The method of any preceding embodiment, wherein said data transmission comprises a command to configure the implantable stimulator circuit, the command being inserted into a packet gap such that forward and reverse data can co-exist without contention while being transmitted entirely via the second inductive coil.

36. The method of any preceding embodiment, further comprising: determining a compliance voltage of the implantable stimulator circuit using a characterized impedance model and known stimulation intensity.

37. The method of any preceding embodiment, wherein stimulation parameters are determined based on the characterized impedance model to ensure an over potential of the electrode array does not exceed a water window of the electrode array.

38. A 176-channel 0.5 cm$^3$ 0.7 g wireless implant for motor function recovery after spinal cord injury and for various medical applications, such as retinal prostheses, gastrointestinal implant, vagus nerve stimulation, and cortical neuromodulation.

39. An epidural spinal stimulator apparatus for motor function recovery, comprising: (a) an implantable stimulator circuit configured for implanting within an organism: (b) an external stimulation circuit configured for retention sufficiently proximal said implantable stimulator circuit for communicating power to said implantable stimulator circuit, and data to and/or from said implantable stimulator circuit; (c) wherein said implantable stimulator circuit comprises: (i) at least one inductive coil configured for receiving power as a power coupling; (ii) at least one inductive coil configured for communicating data as a data coupling; (iii) a data link circuit configured for communicating data through said data coupling; (iv) a flexible epidural electrode array; (v) a multi-channel stimulation circuit having a high voltage output stage configured for multiplexed driving of the electrodes in said epidural electrode array; (vi) a bio-impedance characterization circuit configured for determining bio-impedance at the electrodes of said epidural electrode array; (vii) a multi-channel stimulation recording circuit; (viii) a controller circuit and memory configured for storing stimulation parameters and recorded stimulation data, and for controlling stimulation and communication with the external stimulation circuit; (d) wherein said external stimulation circuit comprises: (i) at least one inductive coil configured for transmitting power as a power coupling to said implantable stimulator circuit; (ii) at least one inductive coil configured for communicating data as a data coupling with said implantable stimulator circuit; (iii) a data link circuit configured for communicating data through said data coupling; (iv) a controller circuit and memory configured for controlling stimulation in said implantable stimulator circuit and for receiving information transmitted by said implantable stimulator circuit.

40. The apparatus of any preceding embodiment, wherein said apparatus is configured for performing simultaneous stimulation and recording.

41. The apparatus of any preceding embodiment, wherein said apparatus is configured for performing real time adjustment of stimulation parameters.

42. The apparatus of any preceding embodiment, wherein said power converter, data transceiver, impedance characterization circuits, and controller circuit of said implantable stimulator circuit are implemented as a system on chip (SoC).

43. The apparatus of any preceding embodiment, further comprising a wireless communications link within said external stimulation circuit, and a remote user control device configured for communicating with said external stimulation circuit.

44. The apparatus of any preceding embodiment, wherein said remote user control device comprises a user interface allowing a user to send stimulation commands and monitor stimulation information from said external stimulation circuit.

45. The apparatus of any preceding embodiment, wherein said user interface of said remote user control device comprises a graphical user interface (GUI).

46. The apparatus of any preceding embodiment, wherein said apparatus provides 160 channels of neural stimulation.

47. The apparatus of any preceding embodiment, wherein said apparatus provides 16 channel recording of neural stimulation.

48. The apparatus of any preceding embodiment, wherein said apparatus provides 48 channels of impedance characterization.

49. An implantable epidural spinal stimulator apparatus for motor function recovery, comprising: (a) at least one inductive coil configured for receiving power as a power coupling within an said implantable stimulator circuit which is configured for receiving power from an external stimulator device; (b) at least one inductive coil configured for communicating data as a data coupling which is configured for communicating data with the external stimulator device; (c) a data link circuit configured for communicating data through said data coupling with the external stimulator device; (d) an epidural electrode array configured for coupling to the neural network of an organism; (e) a multi-channel stimulation circuit having a high voltage output stage configured for multiplexed driving of the electrodes in said epidural electrode array; (f) a bio-impedance characterization circuit configured for determining bio-impedance at the electrodes of said epidural electrode array; (g) a multi-channel stimulation recording circuit; and (h) a controller circuit and memory configured for storing stimulation parameters and recorded stimulation data, and for controlling stimulation and communications with the external stimulation circuit.

50. A method of performing epidural spinal stimulation for motor function recovery, comprising: (a) providing power transmission from an external stimulation circuit and an implanted stimulator circuit; (b) providing data transmission between the external stimulation circuit and an implanted stimulator circuit; (c) generating multi-channel stimulation from an electrode array of said implanted stimulator circuit in which the stimulation parameters can be adjusted in real time; and (d) performing bio-impedance characterization of bio-impedance at the electrode array, wherein said bio-impedance characteristics are utilized for controlling the stimulation applied at said electrode array.

51. A method of performing simultaneously continuous stimulation and recording, wherein during recording, stimuli is fired based on stimulation parameters and triggered by the user specified periodic stimulation signal (Stim_flag).

52. A method to synchronize the recorded data and stimulation from an implant, wherein wireless transmitted data includes both recorded physiological signal and the stimulation onset information (Stim_flag) to enable the synchronization.

53. A method of resetting recording circuits during stimulation onset by selective connecting a Stim_flag to the reset of recording circuits.

54. An array that is embedded in a flexible substrate that connects a SoC and all other necessary components wherein a PCB and a dedicated electrode array are eliminated.

55. A bi-directional data link that adopts DPSK and LSK for forward and reverse data link, respectively.

56. A method of performing full-duplex data link through a communication protocol that allows user to define the data packet size and the time gap between each packet.

57. A method wherein a new command to configure an implant is inserted into a packet gap such that forward and reverse data can co-exist on the same coil without contention.

58. A method of using the characterized impedance model and the known stimulation intensity to determine the compliance voltage of the stimulator, saving the power consumption of an implant.

59. A method of determining the stimulation parameters based on the derived impedance model to ensure the over-potential of the electrode does not exceed the water window of the electrode, preventing irreversible reduction and oxidation at the electrode-electrolyte interface.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An implantable epidural spinal stimulator apparatus for motor function recovery, comprising:
    (a) an implantable stimulator circuit configured for coupling to a neural network of an organism;
    (b) a flexible epidural electrode array coupled to the implantable stimulator circuit comprising a plurality of electrodes;
    (c) wherein said implantable stimulator circuit comprises a controller, memory and application software stored in said memory along with one or more stimulation parameters for:
        (i) generating one or more electrical pulses for epidural electrical stimulation of inter-neurons within the target treatment region to reengage a neural network connecting the brain and spinal cord;
        (ii) receiving bio-impedance data of the target treatment region via the electrode array; and
        (iii) performing real time adjustment of the stimulation parameters as a function of the acquired bio-impedance data.

2. The apparatus of claim 1, wherein the implantable stimulator circuit further comprises a data link circuit configured for communicating data through said data coupling with the external stimulator device.

3. The apparatus of claim 2, wherein the implantable stimulator circuit further comprises a multi-channel stimulation circuit having a high voltage output stage configured for multiplexed driving of the electrodes in said epidural electrode array.

4. The apparatus of claim 3, wherein the implantable stimulator circuit further comprises a bio-impedance characterization circuit configured for determining bio-impedance at the electrodes of said epidural electrode array.

5. The apparatus of claim 4, wherein the implantable stimulator circuit further comprises a multi-channel stimulation recording circuit for acquiring said bio-impedance data.

6. The apparatus of claim 4, wherein said controller circuit, bio-impedance characterization circuit, multi-channel stimulation circuit, data link circuit, and multi-channel stimulation recording circuit of said implantable stimulator circuit are integrated as a system on chip (SoC).

7. The apparatus of claim 6, wherein said flexible epidural electrode array is integrated with the SoC on a singular flexible substrate.

8. The apparatus of claim 1, wherein said implantable stimulator circuit is configured for performing simultaneous stimulation and recording of acquired bio-impedance data.

9. The apparatus of claim 1, wherein said implantable stimulator circuit is configured for performing real time adjustment of stimulation parameters used for providing stimulation of a target treatment region.

10. The apparatus of claim 2, wherein the data link circuit comprises a bi-directional data link that adopts DPSK and LSK for forward and reverse data link, respectively.

\* \* \* \* \*